US011844779B2

United States Patent
Patel et al.

(10) Patent No.: US 11,844,779 B2
(45) Date of Patent: *Dec. 19, 2023

(54) PKC-DELTA-I INHIBITOR FORMULATIONS AND USES THEREOF

(71) Applicants: University of South Florida, Tampa, FL (US); THE UNITED STATES GOVERNMENT AS REPRESENTED BY THE DEPARTMENT OF VETERANS AFFAIRS OFFICE OF GENERAL, Washington, DC (US)

(72) Inventors: Niketa A. Patel, Land O' Lakes, FL (US); Rekha S. Patel, Tampa, FL (US); Robert Pleasants Sparks, Tampa, FL (US); Wayne Charles Guida, Saint Pete Beach, FL (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/472,793

(22) Filed: Sep. 13, 2021

(65) Prior Publication Data

US 2021/0401802 A1 Dec. 30, 2021

Related U.S. Application Data

(63) Continuation of application No. 16/085,221, filed as application No. PCT/US2017/022538 on Mar. 15, 2017, now Pat. No. 11,129,808.

(60) Provisional application No. 62/308,335, filed on Mar. 15, 2016.

(51) Int. Cl.
| | |
|---|---|
| *A61K 31/4035* | (2006.01) |
| *A61K 31/4184* | (2006.01) |
| *A61K 31/444* | (2006.01) |
| *A61K 31/4965* | (2006.01) |
| *A61K 31/36* | (2006.01) |
| *A61K 31/517* | (2006.01) |
| *A61K 45/06* | (2006.01) |
| *A61P 3/04* | (2006.01) |
| *A61K 31/357* | (2006.01) |
| *A61K 31/519* | (2006.01) |

(52) U.S. Cl.
CPC ........ *A61K 31/4035* (2013.01); *A61K 31/357* (2013.01); *A61K 31/36* (2013.01); *A61K 31/4184* (2013.01); *A61K 31/444* (2013.01); *A61K 31/4965* (2013.01); *A61K 31/517* (2013.01); *A61K 31/519* (2013.01); *A61K 45/06* (2013.01); *A61P 3/04* (2018.01)

(58) Field of Classification Search
CPC .. A61K 31/357; A61K 31/36; A61K 31/4035; A61K 31/4184; A61K 31/444; A61K 31/4965; A61K 31/517; A61K 31/519; A61K 45/06; A61P 3/04
See application file for complete search history.

(56) References Cited

U.S. PATENT DOCUMENTS

| | | | |
|---|---|---|---|
| 11,129,808 B2 * | 9/2021 | Patel | .......... A61P 3/04 |
| 2006/0293358 A1 | 12/2006 | Dinsmore et al. | |
| 2007/0072874 A1 | 3/2007 | Cui | |
| 2008/0153903 A1 | 6/2008 | Fleenor | |
| 2011/0082140 A1 | 4/2011 | Dorsch | |
| 2012/0208750 A1 | 8/2012 | Kahn | |
| 2015/0283114 A1 | 10/2015 | Faller | |

OTHER PUBLICATIONS

Alkhouri et al., "Adipocyte Apoptosis, a Link between Obesity, Insulin Resistance, and Hepatic Steatosis", Journal Df Biological Chemistry vol. 285, No. 5, pp. 3428-3439, 2010.
Anantharam et al., Caspase-3-Dependent Proteolytic Cleavage of Protein Kinase Co Is Essential for Oxidative Stress-Mediated Dopaminergic Cell Death after Exposure to Methylcyclopentadienyl Manganese Tricarbonyl, The Journal of Neuroscience, Mar. 1, 2002, 22(5):1738-1751.
Basu et al., "Two Faces of Protein Kinase C.delta.: The Contrasting Roles of PKC? in Cell Survival and Cell Death", TheScientificWorldJournal (2010) 10, 2272-2284.
Bhavanasi et al., "CGX1037 is a novel PKC isoform delta selective inhibitor in platelets", Platelets. 2015 ; 26(1): 2-9. doi:10.3109/09537104.2013.868877.
Blass et al., Tyrosine Phosphorylation of Protein Kinase Co Is Essential for Its Apoptotic Effect in Response to Etoposide, Molecular and Cellular Biology, Jan. 2002, p. 182-195, 2-195, vol. 22, No. 1.
Cho, et al. "Design of a PKCd-specific small peptide as a theragnostic agent for glioblastoma", Analytical Biochemistry 496 (2016) 63-70.
Denning et al., Caspase activation and disruption of mitochondrial membrane potential duringUV radiation-induced apoptosis of human keratinocytes requires activation of protein kinase C:, Cell Death and Differentiation (2002) 9, 40-52.
Emoto et al., "Proteolytic activation of protein kinase C δ by an ICE-like protease in apoptotic cells", The EMBO Journal vol. 14 No. 24 pp. 6148-6156, 1995.
Ghayur et al., "Proteolytic Activation of Protein Kinase Cd by an ICE/CED 3-like Protease Induces Characteristics of Apoptosis", J. Exp. Med., The Rockefeller University Press .cndot. 0022-1007/96/12/2399/06 $2.00, vol. 184 Dec. 1996 pp. 2399-2404.
International Search Report for PCT/US2017/022538 dated Jun. 12, 2017.

(Continued)

*Primary Examiner* — Kara R McMillian
(74) *Attorney, Agent, or Firm* — Quarles & Brady LLP

(57) ABSTRACT

Provided herein are formulations that can contain an effective amount of a PKCδ inhibitor. Also provided herein are methods of inhibiting a PKCδ in a subject in need thereof, that can include the step of administering an effective amount of a compound that is capable of inhibiting a PKCδ.

4 Claims, 7 Drawing Sheets

(56) References Cited

OTHER PUBLICATIONS

Kawaguchi et al., "New PKCd family members, PKCdIV, dV, dVI, and dVII are specifically expressed in mouse testis", EBS Letters 580 (2006) 2458-2464.
King, et al. 'a, B-Unsaturated Hydroxyketones', Journal of Chemical & Engineering Data, Oct. 1968, vol. 13, p. 565-566; p. 565.
Merour, et al. The Azaindole Framework in the Design of Kinase Inhibitors', Molecules, Nov. 28, 2014 (Nov. 28, 2014), vol. 19, p. 19935-19979; p. 19935.
National Center for Biotechnology Information. PubChem Database. SID 5302180, Source=ChemDB, SID=5302180, https://pubchem.ncbi.nlm.nih.gov/substance/5302180 (Year: 2005).
Parker, et al., "Cell Science at a Glance", PKC at a glance Journal of Cell Science 117, 131-132 Published by The Company of Biologists 2004 doi:10.1242/jcs.00982.
Patel et al., PKC.delta. Alternatively Spliced Isoforms Modulate Cellular Apoptosis in Retinoic Acid-Induced Differentiation of Human NT2 Cells and Mouse Embryonic Stem Cells, Gene Expression, vol. 13, pp. 73-84 105.
Patel et al., Protein Kinase C delta ( dulate apoptosis pathway in 3T3L1 cells during adipogenesis: Identification of PKC.delta.II inhibitor, J. Biol. Chem. published online Jul. 31, 2013.
Patel, "Transformer 2J3 homolog (*Drosophila*) (TRA2B) Regulates Protein Kinase C 6I (PKC6I) Splice Variant Expression during 3T3L1 Preadipocyte Cell Cycle*" The Journal of Biological Chemistry vol. 289, No. 16, p. 31662-31672, Nov. 14, 2014.
Pubmed CID 17534685, 'MolPort-005-662-260', U.S. National Library of Medicine, Nov. 13, 2007 (Nov. 13, 2007), (https://pubchem.ncbi.nlm.nih.gov/compound/17534685); p. 3.
Pubmed CID 3662572, '1-Penten-3-one, 1-(1,3-benzodioxol-5-yl)-4-hydroxy-4-methyl-', U.S. National Library of Medicine, Sep. 10, 2005 (Sep. 10, 2005), (https://pubchem.ncbi.nlm.nih.gov/compound/3662572); p. 2.
Pubmed CID 3764448, 'AC1MXEPO', U.S. National Library of Medicine, Sep. 10, 2005 (Sep. 10, 2005), (https://pubchem.ncbi.nlm.nih.gov/compound/3764448); p. 3.
Pubmed CID 45596959, 'Ambcb5139627', U.S. National Library of Medicine, Sep. 10, 2005 (Sep. 10, 2005), (https://pubchem.ncbi.nlm.nih.gov/compound/45596959); p. 3.
Pubmed CID 46529198, 'CID 46529198', U.S. National Library of Medicine, Jul. 23, 2010 (Jul. 23, 2010), (https://pubchem.ncbi.nlm.nih.gov/compound/46529198); p. 3.
Pubmed CID 50961980, 'MolPort-016-606-250', U.S. National Library of Medicine, Mar. 29, 2011 (Mar. 29, 2011), (https://pubchem.ncbi.nlm.nih.gov/compound/50961980); p. 3.
Pubmed CID 56867286, 'MolPort-020-199-812', U.S. National Library of Medicine, Mar. 30, 2012 (Mar. 30, 2012), (https://pubchem.ncbi.nlm.nih.gov/compound/56867286); p. 3.
Pubmed CID 56878311, 'MCULE-2074820729', U.S. National Library of Medicine, Mar. 30, 2012 (Mar. 30, 2012), (http://pubchem.ncbi.nlm.nih.gov/compound/56878311); p. 3.
Pubmed CID 56888951, 'ZINC72137086', U.S. National Library of Medicine, Mar. 30, 2012 (Mar. 30, 2012), (https://pubchem.ncbi.nlm.nih.gov/compound/56888951); p. 3.
Pubmed CID 56902500, 'ZINC72147050', U.S. National Library of Medicine, Mar. 30, 2012 (Mar. 30, 2012), (https://pubchem.ncbi.nlm.nih.gov/compound/56902500); p. 3.
Pubmed CID 56907689, 'MolPort-020-219-811-4', U.S. National Library of Medicine, Mar. 30, 2012 (Mar. 30, 2012), (https://pubchem.ncbi.nlm.nih.gov/compound/56907689); p. 3.
Pubmed CID 5888996, 'ZINC00210538', U.S. National Library of Medicine, Sep. 10, 2005 (Sep. 10, 2005), (http://pubchem.ncbi.nlm.nih.gov/compound/5888996);p. 3.
Pubmed CID 7693840, '3-(1H-benzimidazol-2-yl)-N-(3-phenylpropyl)propanamide', U.S. National Library of Medicine, Jul. 29, 2006 (Jul. 29, 2006), (https://pubchem.ncbi.nlm.nih.gov/compound/7693840); p. 3.
Qvit et al., "The many hats of protein kinase C.delta.: one enzyme with many functions", Biochem. Soc. Trans. (2014) 42, 1529-1533; doi:101042/BST20140189.
Reyland et al., "Multifunctional roles of PKC.delta.: Opportunities for targeted therapy in human disease", http://dx.doi.org/10.1016, Pharmacology & Therapeutics 165 (2016) 1-13.
Reyland et al., "Protein Kinase C d Is Essential for Etoposide-induced Apoptosis in Salivary Gland Acinar Cells*", The Journal of Biological Chemistry vol. 274, No. 27, Issue of Jul. 2, pp. 19115-19123, 1999 .COPYRGT. 1999 by The American Society for Biochemistry and Molecular Biology, Inc., http://www.jbc.org.
Sakurai et al., "Novel Protein Kinase C d Isoform Insensitive to Caspase-3", Department of Biochemistry, Tokyo Dental College,a 1-2-2 Masago, Mihama-ku, Chiba 261-8502, Japan, and Institute of Molecular and Cell Biology, AIST,b 1-1 Higash, Tsukuba, Ibaraki 305-8566, Japan., Biol. Pharm. Bull. 24(9) 973-977 (2001).
Sampson, et al., "Specific protein kinase C isoforms as transducers and modulators of insulin signaling".
Sitailo et al., "Bax Activation and Induction of Apoptosis in Human Keratinocytes by the Protein Kinase C d Catalytic Domain", Department of Pathology and the Oncology Institute, Skin Cancer Research Program, Loyola University Medical Center, Maywood, Illinois, USA, pp. 434-443.
Sitalio et al. The Protein Kinase C.delta. Catalytic Fragment Targets Mcl-1 for Degradation to Trigger Apoptosis*, From the Department of Pathology and the Oncology Institute, Skin Cancer Research Program, Loyola University Medical Center, Maywood, Illinois 60153, pp. 1-16.
Sparks et al. A specific small-molecule inhibitor of Protein Kinase C.delta.I activity improves metabolic dysfunction in human adipocytes from obese individuals, http://www.jbc.org/, JBC Papers in Press. Published on Aug. 14, 2019 as Manuscript RA119.008777, pp. 1-24.
Steinberg et al., Distinctive activation mechanisms and functions for protein kinase C.delta., Biochem. J. (2004) 384, 449-459 (Printed in Great Britain).
Ueyama et al., "cDNA Cloning of an Alternative Splicing Variant of Protein Kinase C 3 (PKC 3III), a New Truncated Formof PKC3, in Rats", Biochemical and Biophysical Research Communications 269, 557-563 (2000), doi:10.1006/bbrc.2000.2331, available online at http://www.idealibrary.com.
Xia et al., Phosphoproteomics Study on the Activated PKC.delta.-Induced Cell Death, Journal of Proteome Research, 201 American Chemical Society, J. Proteome Res. 2013, 12, 4280-4301.

* cited by examiner

In-vitro kinase assay
Using pure protein PKCdI and MBP

PKC-DELTA-I INHIBITOR FORMULATIONS AND USES THEREOF

CROSS-REFERENCE TO RELATED APPLICATIONS

This application is a continuation of U.S. patent application Ser. No. 16/085,221, filed Sep. 14, 2018, which is a national stage filing under 35 U.S.C. § 371 of International Application No. PCT/US2017/022538, filed Mar. 15, 2017, which claims the benefit of and priority to U.S. Provisional Patent Application No. 62/308,335, filed on Mar. 15, 2016, entitled "SMALL MOLECULE INHIBITOR OF PKC I AS THERAPEUTIC APPLICATION IN OBESITY, DIABETES, INSULIN RESISTANCE, AND METABOLIC SYNDROME," the contents of each are incorporated by reference herein in their entirety.

STATEMENT REGARDING FEDERALLY SPONSORED RESEARCH OR DEVELOPMENT

This invention was made with government support under grant number awarded by the Veterans Affairs. The government has certain rights in the invention.

BACKGROUND

Obesity, diabetes, cancer, osteoarthritis, hepatosteatosis, cardiovascular diseases and metabolic syndrome are all significant health issues, particularly in developed countries. The causes are complex and there are relatively limited therapeutic and preventative pharmaceuticals. As such, there exists a need for improved pharmaceuticals for treating and preventing these diseases or symptoms thereof.

SUMMARY

In some aspects, provided herein are methods of treating a PKCδI disease or disorder in a subject in need thereof, that can include administering a pharmaceutical formulation comprising an effective amount of a PKCδI inhibitor to the subject in need thereof, wherein the PKCδI inhibitor is a compound having a structure as in any one of Formulas 1 and 3-7

Formula 1

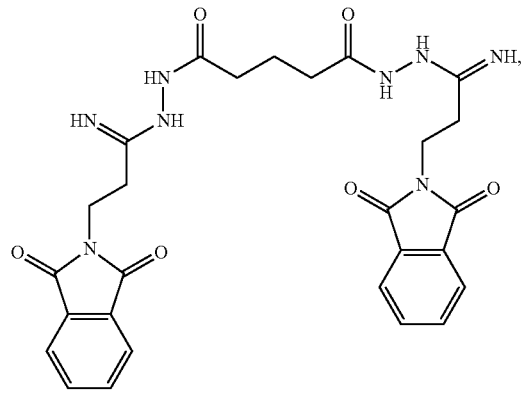

-continued

Formula 3

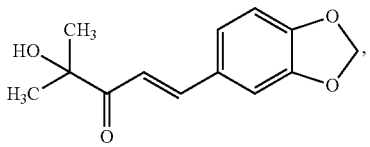

Formula 4

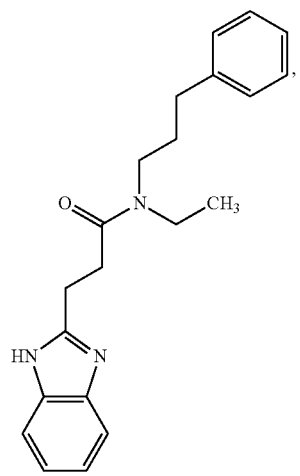

Formula 5

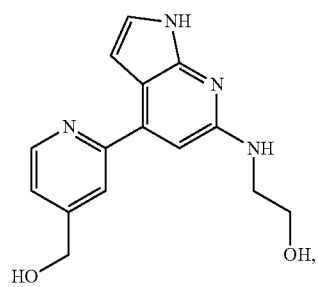

Formula 6

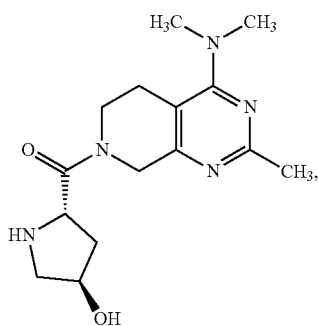

Formula 7

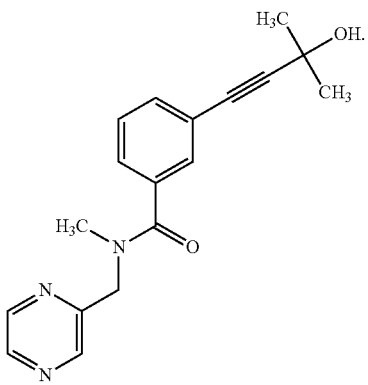

The PKCδI inhibitor can be effective to reduce PKCδI activity in the subject in need thereof. The PKCδI inhibitor can be effective to reduce PKCδI activity in an adipocyte in the subject in need thereof. The PKCδI inhibitor can be a compound according to Formula 1. The PKCδI inhibitor can be effective to reduce activity of PKCδI and is not effective to reduce the activity of PKCα, PKCβ, PKCγ, PKCε, PKCθ, PKCI, PKCζ PKCδII, PKCδVIII or any combination thereof. In some aspects, PKCδI inhibitor can simultaneously bind the DMQD amino acid sequence within the V3 hinge region of PKCδI and the active site on the C2 domain of PKCδI. The PKCδI disorder can be diabetes, a cancer, an inflammatory, disease obesity, insulin resistance, metabolic syndrome hepatosteatosis, a cardiovascular disease, a neurodegenerative disease or a symptom thereof. The effective amount of the PKCδI inhibitor can range from about 0.001 micrograms to about 1 g.

In some aspects, provided herein are methods of reducing adipocyte apoptosis in a subject in need thereof that can include the step of administering a pharmaceutical formulation comprising an effective amount of PKCδI inhibitor to the subject in need thereof, wherein the PKCδI inhibitor is a compound having a Formula as in any one of Formulas 1 and 3-7

Formula 1

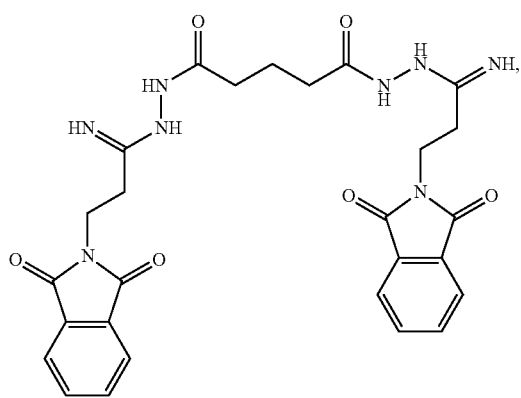

Formula 3

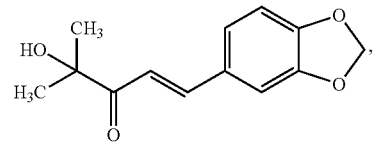

Formula 4

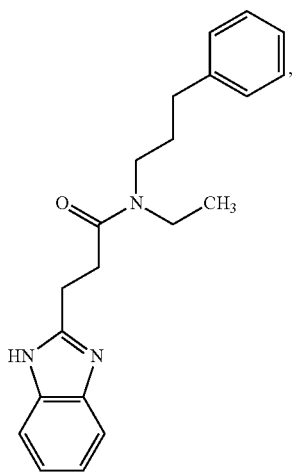

Formula 5

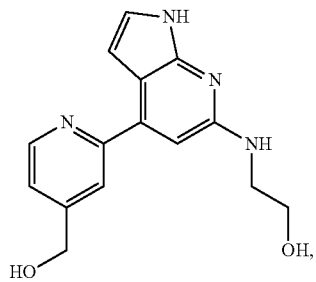

Formula 6

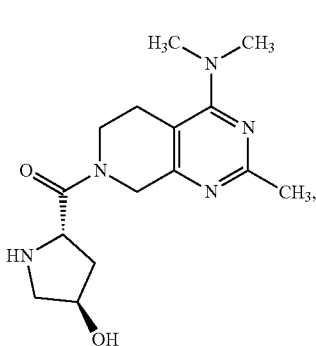

Formula 7

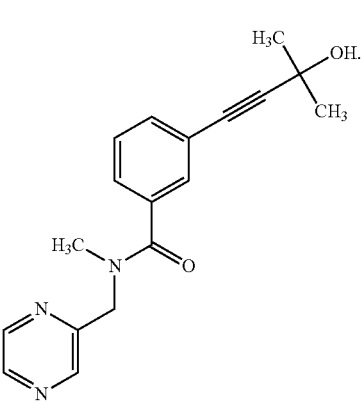

The PKCδI inhibitor can be effective to reduce PKCδI activity in the subject in need thereof. The PKCδI inhibitor can be effective to reduce PKCδI activity in an adipocyte in the subject in need thereof. The PKCδI inhibitor is a compound according to Formula 1. The PKCδI inhibitor can be effective to reduce the activity of PKCδI and is not effective to reduce the activity of PKCα, PKCβ, PKCγ, PKCε, PKCθ, PKCI, PKCζ PKCδII, PKCδVIII or any combination thereof. The PKCδI inhibitor can simultaneously bind the DMQD amino acid sequence within the V3 hinge region of PKCδI and the active site on the C2 domain of PKCδI. The subject in need thereof can have diabetes, a cancer, an inflammatory, disease obesity, insulin resistance, metabolic syndrome hepatosteatosis, a cardiovascular disease, a neurodegenerative disease or a symptom thereof.

Also provided herein are pharmaceutical formulations that can have an amount of a PKCδI inhibitor, wherein the amount can be an effective amount that can reduce PKCδI activity in a subject, and wherein the PKCδI inhibitor can be a compound having a Formula as in any one of Formulas 1 and 3-7

Formula 1

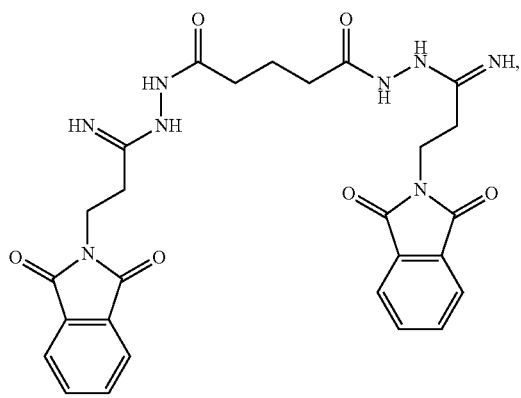

Formula 3

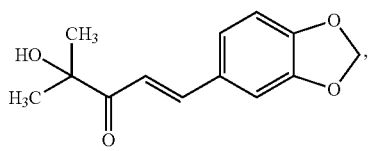

Formula 4

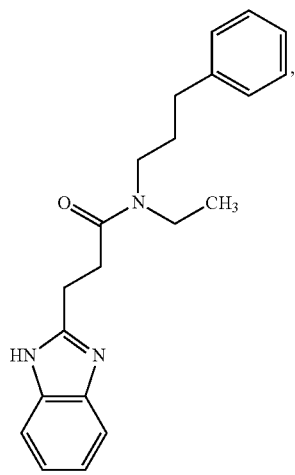

Formula 5

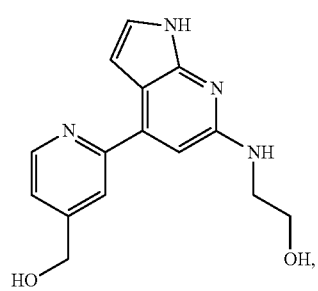

Formula 6

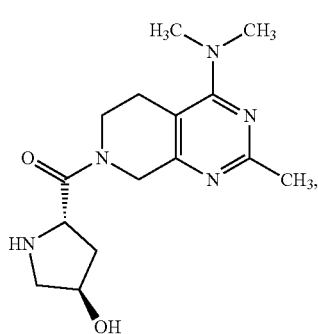

Formula 7

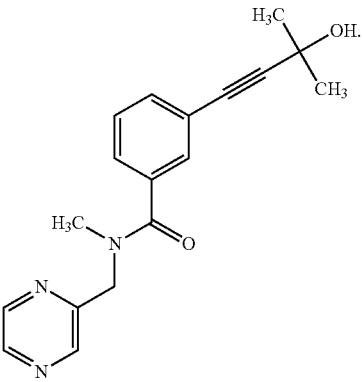

The PKCδI inhibitor can be a compound according to Formula 1. In some aspects, the effective amount of the PKCδI inhibitor is not effective to reduce the activity of PKCα, PKCβ, PKCγ, PKCε, PKCθ, PKCI, PKCζ PKCδII, PKCδVII or any combination thereof. The effective amount of the PKCδI inhibitor can simultaneously bind the DMQD amino acid sequence within the V3 hinge region of PKCδI and the active site on the C2 domain of PKCδI. The effective amount of the PKCδI inhibitor can be effective to reduce adipocyte apoptosis. The effective amount of the PKCδI inhibitor can be effective to treat or prevent diabetes, a cancer, an inflammatory, disease obesity, insulin resistance, metabolic syndrome hepatosteatosis, a cardiovascular disease, a eurodegenerative disease, or a symptom thereof.

In some aspects, provided herein are methods of treating a PKCδI disease or disorder in a subject in need thereof that can include the step of administering a pharmaceutical formulation comprising an effective amount of a PKCδI inhibitor to the subject in need thereof, wherein the PKCδI inhibitor is a compound having a structure as in Formula 1 or a structural analogue thereof, wherein the structural analogue can specifically bind the DMQD amino acid sequence within the V3 hinge region of PKCδI or simultaneously bind the DMQD amino acid sequence within the V3 hinge region of PKCδI and the active site of PKCδI on the C2 domain of PKCδI. The PKCδI inhibitor can be effective to reduce activity of PKCδI and is not effective to reduce the activity of PKCα, PKCβ, PKCγ, PKCε, PKCθ, PKCI, PKCζ PKCδII, PKCδVIII or any combination thereof. The PKCδI disorder can be diabetes, a cancer, an inflammatory, disease obesity, insulin resistance, metabolic syndrome hepatosteatosis, a cardiovascular disease, a neurodegenerative disease, or a symptom thereof.

In some aspects, also provided herein are methods of reducing PKCδI expression in a subject in need thereof that can include administering a pharmaceutical formulation comprising an effective amount of a PKCδI inhibitor to the subject in need thereof, wherein the PKCδI inhibitor is a compound having a structure as in Formula 1

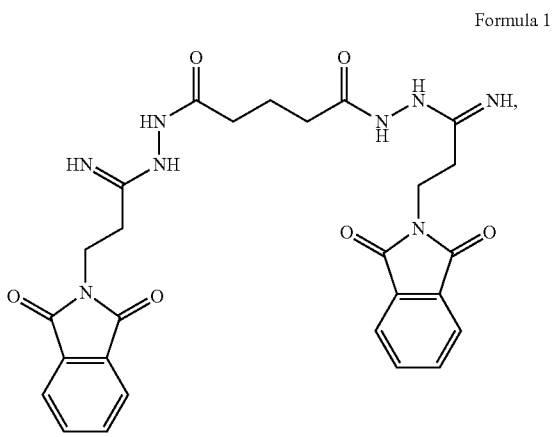 [SMILES: N=C(CCN1C(=O)c2ccccc2C1=O)NNC(=O)CCCC(=O)NNC(=N)CCN1C(=O)c2ccccc2C1=O]

Formula 1 or a structural analogue thereof, wherein the structural analogue can specifically bind the DMQD amino acid sequence within the V3 hinge region of PKCδI or simultaneously bind the DMQD amino acid sequence within the V3 hinge region of PKCδI and the active site of PKCδI on the C2 domain of PKCδI. In some embodiments, PKCδI expression is reduced in an adipocyte in a subject in need thereof after administration of the PKCδI inhibitor. The PKCδI inhibitor can be effective to reduce activity of PKCδI and is not effective to reduce the activity of PKCα, PKCβ, PKCγ, PKCε, PKCθ, PKCI, PKCζ, PKCδII, PKCδVIII or any combination thereof. The subject in need thereof can have a PKCδI disorder. The subject in need thereof can have diabetes, a cancer, an inflammatory, disease obesity, insulin resistance, metabolic syndrome hepatosteatosis, a cardiovascular disease, a neurodegenerative disease or a symptom thereof.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
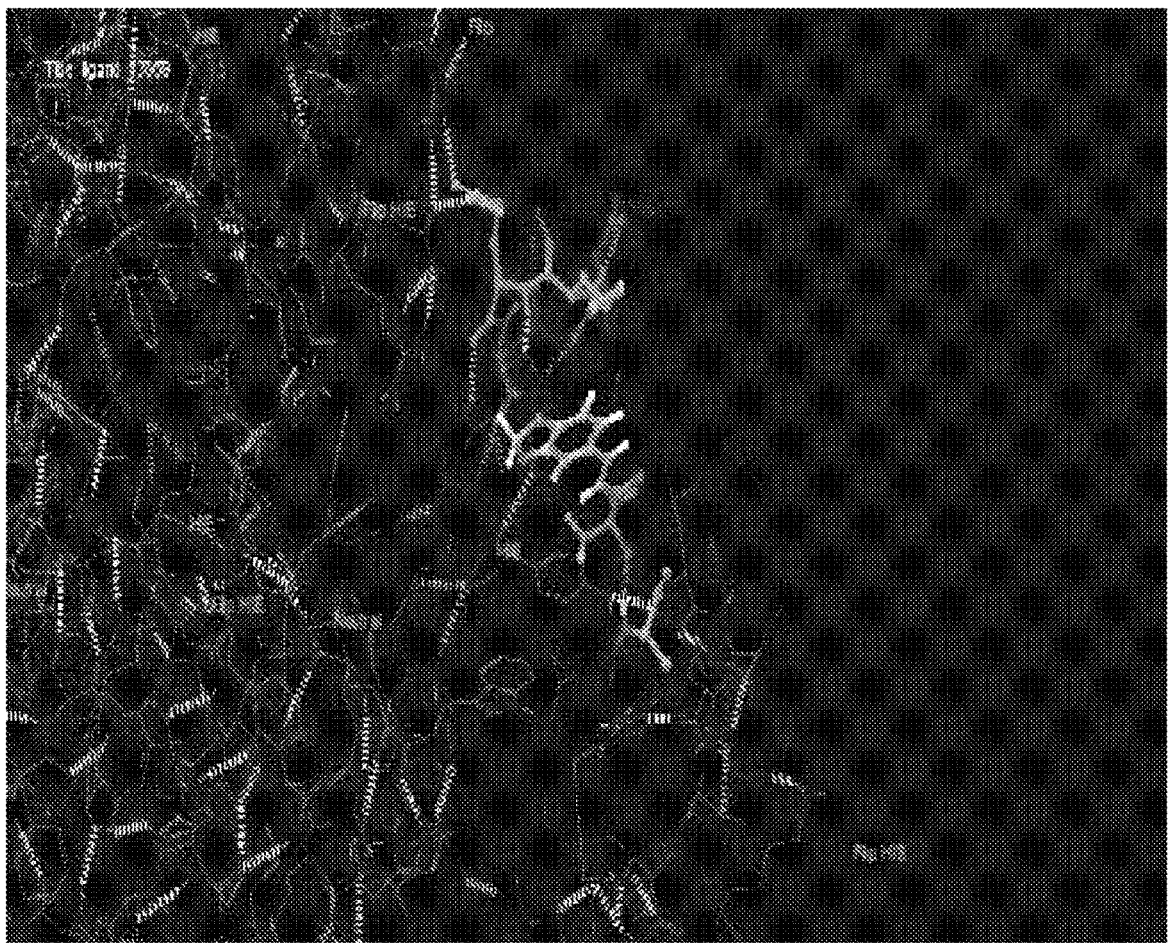
FIG. 1 shows an example modeling of docking PKCδI demonstrating compound 5320091 docked to the DMQD region of PKCδI.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, chemistry, organic chemistry, biochemistry, pharmacology, and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "administering" can refer to any administration route, including but not limited to administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, inter nasal, intrathecal, intrahepatic, intralesional, and intracranial injections or infusion techniques.

As used interchangeably herein, "biocompatible," "biocompatibility," and "biologically compatible" refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "cancer" can refer to any disease with in the collection of related diseases whose etiology and/or pathology involve abnormal cell growth and proliferation that can include invasion into surrounding and/or distant tissues. Cancerous tumors can be malignant or benign.

As used herein, "chemotherapeutic" refers to a chemical compound or agent used to treat, control, or cure a disease or symptoms thereof, particularly cancer.

As used herein, "composition" or "formulation" can refer to a combination of an active agent(s) and another compound or composition, inert (for example, a detectable agent or label) or active, such as an adjuvant.

As used herein, "a compound of formula (1), (2), (3), (4), (5), (6), (7), (8), (9), (10), (11), (12), (13), (14), and so forth and so on," or "a compound having a structure according to formula (1), (2), (3), (4), (5), (6), (7), (8), (9), (10), (11), (12), (13), (14), and so forth and so on" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "control" can refer to an alternative subject or sample used in an experiment for comparison purposes and included to minimize or distinguish the effect of variables other than an independent variable. A control can be positive or negative.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" when used in reference to an amount of a molecule, compound, or composition including but not limited to, a chemical compound, polynucleotide, peptide, polypeptide, protein, antibody, or fragments thereof, can indicate that the sample is distinguishable from its naturally occurring counterpart in that the concentration or number of molecules per volume is less than that of its naturally occurring counterpart.

As used herein, "effective amount" is an amount sufficient to effect beneficial or desired results. An effective amount can be administered in one or more administrations, applications, or dosages. "Effective amount" can refer to an amount of a PKCδI inhibitor provided herein (e.g. a compound according to any one of Formulas 1 and 3-7 or a structural analogue thereof) that can reduce the amount of PKCδI activity, which can be measured using a suitable assay (including, but not limited to, a kinase assay). Structural analogues of a PKCδI inhibitor provided herein are those structural analogues that specifically bind the DMQD amino acid sequence within the V3 hinge region of PKCδI or simultaneously bind the DMQD amino acid sequence within the V3 hinge region of PKCδI and the active site of PKCδI on the C2 domain of PKCδI. "Effective amount" can refer to an amount of a PKCδI inhibitor provided herein that can reduce the amount of PKCδI activity without reducing the amount or affecting the activity and/or amount PKCα, PKCβ, PKCγ, PKCε, PKCθ, PKCI, PKCζ PKCδII, PKCδVIII or any combination thereof. "Effective amount" can refer to an amount of a PKCδI inhibitor provided herein that can reduce apoptosis, restore apoptosis to non-diseased levels, in a subject. "Effective amount" can refer to an amount of a PKCδI inhibitor provided herein that can reduce adipocyte apoptosis and/or restore adipocyte apoptosis to non-diseased levels, in a subject having a PKCδI disorder. "Effective amount" can refer to an amount of a PKCδI inhibitor that can treat or prevent a PKCδI disorder or symptom thereof in a subject. "Effective amount" can refer to an amount of a PKCδI inhibitor that can treat or prevent diabetes, cancer, an inflammatory disease (such as osteoarthritis), obesity, insulin resistance, metabolic syndrome hepatosteatosis, a cardiovascular disease, neurodegenerative diseases or a symptom thereof. The "effective amount" can also refer to the least amount sufficient to effect beneficial or desired results, which are discussed above.

As used herein, "hydrate" refers to a compound formed by the addition of water. Typically, but not always, this will be crystalline lattice structures that incorporate water molecules. Hydrates include stoichiometric hydrates, as well as compositions containing variable amounts of water.

As used herein, "metabolic syndrome" can refer to a group of metabolic risk factors such as hyperglycemia, hypertension, insulin resistance, and cholesterol abnormalities, which increase the risk for cardiovascular diseases and type 2 diabetes.

As used herein, "mitigate" can refer to reducing a particular characteristic, symptom, or other biological or physiological parameter associated with a disease or disorder.

As used herein, "obese" can refer to the condition of a subject where a subject has a Body mass index (BMI) of greater than about 30. BMI is calculated as the individual's weight on kilograms divided by height in meters squared.

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein "pharmaceutically effective amount" can refer to an amount of a compound or formulation thereof provided herein that can prevent diabetes, cancer, an inflammatory disease (such as osteoarthritis), obesity, insulin resistance, metabolic syndrome hepatosteatosis, a cardiovascular disease, neurodegenerative diseases or a symptom thereof. In embodiments, the "pharmaceutically effective amount" can be the least amount of a compound or formulation thereof provided herein needed to treat, prevent, or elicit the desired biological and/or medical effect in the response of a cell, tissue, organ, system, or subject that is being sought by the researcher, veterinarian, medical doctor or other clinician as described above. In some embodiments, the "pharmaceutically effective amount" can be the least amount that can treat or prevent diabetes, cancer, an inflammatory disease (such as osteoarthritis), obesity, insulin resistance, metabolic syndrome hepatosteatosis, a cardiovascular disease, neurodegenerative diseases or a symptom thereof. "Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician as discussed above. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" refers to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "PKCδ1 disorder" refers to a disease or disorder whose etiology and/or pathology includes up-regulation or increased expression (as compared to a normal or non-diseased control) of PKCδ1 in adipocytes and/or other cells. Example diseases and disorders can include, but are not limited to diabetes, cancer, an inflammatory disease (such as osteoarthritis), obesity, insulin resistance, metabolic syndrome hepatosteatosis, a cardiovascular disease, a neurodegenerative disease or a symptom thereof.

As used herein, "PKCδ1-specific inhibitor" can refer to a compound that can specifically bind PKCδ1 and not PKCα, PKCβ, PKCγ, PKCε, PKCθ, PKCI, PKCζ PKCδII, PKCδVIII or any combination thereof. The term "PKCδ1-specific inhibitor" can refer to a compound that can reduce PKCδ1 activity and not reduce and/or effect the activity of PKCα, PKCβ, PKCγ, PKCε, PKCθ, PKCI, PKCζ PKCδII, PKCδVIII or any combination thereof. The term "PKCδ1-specific inhibitor" can refer to a compound that can bind the DMQD amino acid sequence within the V3 hinge region of PKCδI or simultaneously bind the DMQD amino acid sequence within the V3 hinge region of PKCδI and the active site of PKCδI on the C2 domain of PKCδI.

As used herein, "preventative," "preventing," "prevent" and the like refer to partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to prevent diabetes, cancer, an inflammatory disease (such as osteoarthritis), obesity, insulin resistance, metabolic syndrome hepatosteatosis, a cardiovascular disease, a neurodegenerative diseases or a symptom thereof.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(14) or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-6}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include aptamer-aptamer target interactions, antibody-antigen interactions, avidin-biotin interactions, ligand-receptor interactions, metal-chelate interactions, hybridization between complementary nucleic acids, etc.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic", "treating", "treat" and the like can refer to include partially or completely delaying, alleviating, mitigating or reducing the intensity of one or more attendant symptoms of a disease or condition including, but not limited to, diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

As used herein, "$C_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O— alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

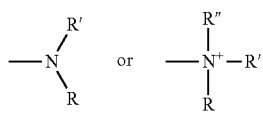

wherein R, R', and R" each independently represent a hydrogen, an alkyl, an alkenyl, —(CH2)$_m$—R$_c$ or R and R' taken together with the N atom to which they are attached complete a heterocycle having from 4 to 8 atoms in the ring structure; R$_c$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

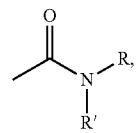

wherein R and R' are as defined above.

As used herein, "Aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

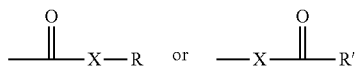

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, (C3-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optically substituted" can indicate that a group may be unsubstituted or substituted with one or more substituents as defined herein.

Discussion

Protein kinase C (PKC), a serine/threonine kinase family, consists of 11 isoforms and their splice variants and is involved in the regulation of cellular differentiation, growth and apoptosis. PKCs have an N-terminal regulatory domain and a C-terminal catalytic domain, which are separated from one another by a hinge region. PKCs, including PKCδI, can be activated upon binding of an activating factor (e.g. calcium, phosphatidyl serine, diacyl glycerol or phorbol esters, which results in the release of a pseudosubtrate region (present in the regulatory domain) from the substrate binding pocket of the catalytic domain that it normally occupies when no activating factor is present. PKCs, including PKCδI, can also be activated by cleavage at the hinge region by an enzyme, which results in a constitutively active catalytic domain of the PKC.

Obesity, diabetes, cancer, osteoarthritis, hepatosteatosis, cardiovascular diseases and metabolic syndrome are all significant health issues, particularly in developed countries. Despite their varying etiologies and pathologies, PKCδI is upregulated in these diseases and disorders. PKCδI plays a central role in promoting apoptosis, particularly in adipocytes. Adipocyte death has been linked to obesity, metabolic disorders, including insulin resistance, hepatic steatosis, and inflammation, which may be mediated by PKCδI. PKC delta inhibitors, particularly PKCδI specific inhibitors may be useful for treating these and related diseases and disorders. However, such compounds are limited and due to their relative non-specificity, can have undesirable side effects. Further, there are currently no known PKCδI-specific inhibitors.

With this in mind, described herein are PKCδ, including PKCδI-specific inhibitors and formulations that can contain an effective amount of a PKCδ, such as a PKCδI-specific inhibitor. Also provided herein are methods of inhibiting PKCδ, including specifically inhibiting PKCδI, by administering a PKCδ inhibitor, such as a PKCδI-specific inhibitor, to a subject in need thereof. In some aspects, the subject can be obese Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Pharmaceutical Formulations of PKCδ Inhibitors

Provided herein are pharmaceutical formulations that can contain an amount of a compound having a structure to any one of Formulas 1-7 or a structural analogue thereof and a pharmaceutically acceptable carrier.

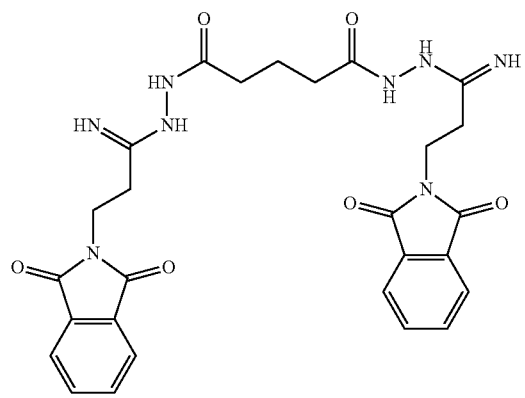

Formula 1

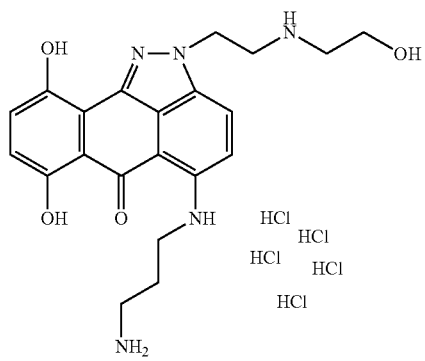

Formula 2

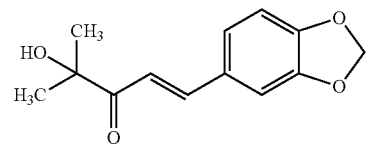

Formula 3

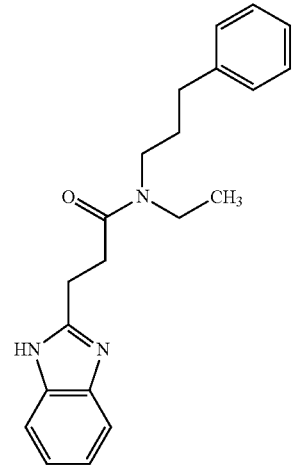

Formula 4

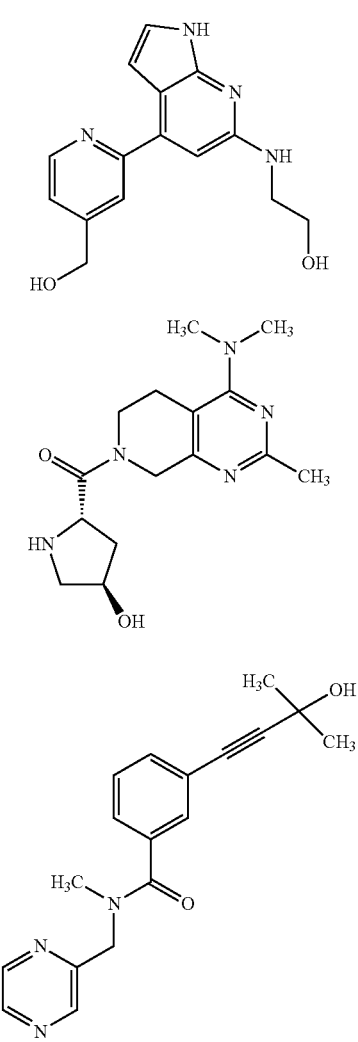

Formula 5

Formula 6

Formula 7

Also provided herein are pharmaceutical formulations that can include and amount, such as an effective amount, least effective amount, and/or a pharmaceutically effective amount of a PKCδ inhibitor, such as a PKCδI-specific inhibitor. In some aspects that pharmaceutical formulation can include one or more of any one of compounds having a structure according to any one of formulas 1 and 3-7 or a structural analogue thereof. In some aspects, a PKCδ inhibitor can have a structure according to any one of formulas, 1 and 3-7. In some aspects, a PKCδI inhibitor can have a structure according to any one of formulas 1 and 3-7 or a structural analogue thereof. In some aspects, a PKCδI-specific inhibitor can have a structure according to formula 1 or a structural analogue there of that can specifically bind the DMQD amino acid sequence within the V3 hinge region of PKCδI. In some aspects, the PKCδI-specific inhibitor or structural analogue thereof can simultaneously bind the the DMQD amino acid sequence within the V3 hinge region of PKCδI and the active site of PKCδI on the C2 domain of PKCδI.

The compounds described herein can be provided to a subject in need thereof as an ingredient, such as an active ingredient, in a pharmaceutical formulation. As such, also described are pharmaceutical formulations containing one or more of the compounds and salts thereof, or pharmaceutically acceptable salts thereof described herein. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations or salts thereof can be administered to a subject in need thereof. In some aspects, the subject has a disease or disorder in which PKCδI protein and/or RNA is up-regulated as compared to a non-diseased control as measured by a suitable assay. In some aspects, the subject has a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some aspects, the subject has diabetes, cancer, an inflammatory disease (such as osteoarthritis), obesity, insulin resistance, metabolic syndrome hepatosteatosis, a cardiovascular disease, or a symptom thereof. In embodiments, the compounds described herein are used in the manufacture of a medicament for the treatment of diabetes, cancer, an inflammatory disease (such as osteoarthritis), obesity, insulin resistance, metabolic syndrome hepatosteatosis, a cardiovascular disease, a neurodegenerative diseases or a symptom thereof.

Pharmaceutically Acceptable Carriers and Auxiliary Ingredients and Agents

The pharmaceutical formulations containing an amount, such as an effective amount, least effective amount, and/or pharmaceutically effective amount of a compound described herein or a derivative thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In addition to the effective amount of a compound and/or derivative thereof, the pharmaceutical formulations can also include an effective amount of auxiliary active agents, including but not limited to, antisense or RNA interference molecules, chemotherapeutics, or antineoplasic agents, hormones, antibiotics, antivirals, immunomodulating agents, antinausea, pain modifying compounds (such as opiates), anti-inflammatory agents, antipyretics, antibiotics, and/or antibodies or fragments thereof.

Effective Amounts of the PKCδ Inhibitors and Auxiliary Active Agents

In some aspects, the effective amount, least effective amount, and/or pharmaceutically effective amount of the PKCδ inhibitor having a Formula according to any one of Formulas 1 and 3-7 or a structural analogue thereof can inhibit PKCδI without inhibiting PKCδII. In some aspects, the effective amount, least effective amount, and/or pharmaceutically effective amount of the PKCδI-specific inhibitor that can have a Formula according to Formula 1 can inhibit PKCδI activity without inhibiting PKCα, PKCβ, PKCγ, PKCε, PKCθ, PKCI, PKCζ PKCδII, and/or PKCδVIII, The effective amount, least effective amount, and/or pharmaceutically effective amount of the compound or PKCδ inhibitor that can have a structure according to any one of Formulas 1-7 or a structural analogue thereof contained in the pharmaceutical formulation can range from about 0.001 micrograms to about 1000 grams, about 0.01 micrograms to about 100 grams, about 0.1 micrograms to about 10 grams, or about 1 microgram to about 1 gram, about 10 micrograms to about 100 mg, 100 micrograms to about 10 mg, or about 1 mg to about 5 mg. In some embodiments, the effective concentration can range from about 1 pM to about 100 nM, about 10 pM to about 10 nM, or about 100 pm, to about 1 nM.

In embodiments where there is an auxiliary active agent contained in the compound or derivative thereof pharmaceutical formulation, the effective amount of the auxiliary active agent will vary depending on the auxiliary active agent. In some embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total pharmaceutical formulation.

The auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total auxiliary active agent pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total auxiliary agent pharmaceutical formulation.

Dosage Forms

In some embodiments, the pharmaceutical formulations described herein can be in a dosage form. The dosage form can be administered to a subject in need thereof. In some aspects, the subject can have a disease or disorder in which PKCδI protein and/or RNA is up-regulated as compared to a non-diseased control as measured by a suitable assay. In some aspects, the subject can have a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative disease or a symptom thereof.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution.

The oral dosage form can be administered to a subject in need thereof. In some aspects, the subject can have a disease or disorder in which PKCδI protein and/or RNA is up-regulated as compared to a non-diseased control as measured by a suitable assay. In some aspects, the subject can have a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative diseases or a symptom thereof.

Where appropriate, the dosage forms described herein can be microencapsulated. The dosage form can also be prepared to prolong or sustain the release of any ingredient. In some embodiments, a compound of Formulas 1-7 or a structural analogue thereof, a PKCδ inhibitor according to any one of Formulas 1 and 3-7 or a structural analogue thereof, a PKCδI-specific inhibitor according to Formula 1, auxiliary active ingredient, and/or pharmaceutically acceptable salt thereof can be the ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound of Formulas 1-7 or a structural analogue thereof, a PKCδ inhibitor according to any one of Formulas 1 and 3-7 or a structural analogue thereof, a PKCδI-specific inhibitor according to Formula 1, auxiliary active ingredient, and/or pharmaceutically acceptable salt thereof can be integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation.

The liposomal formulation can be administered to a subject in need thereof. In some aspects, the subject can have a disease or disorder in which PKCδI protein and/or RNA is up-regulated as compared to a non-diseased control as measured by a suitable assay. In some aspects, the subject can have a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative disease or a symptom thereof.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, a compound of Formulas 1-7 or a structural analogue thereof, a PKCδ inhibitor according to any one of Formulas 1 and 3-7 or a structural analogue thereof, a PKCδI-specific inhibitor according to Formula 1 or a structural analogue thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

The nasal/inhalation formulations can be administered to a subject in need thereof. In some aspects, the subject can have a disease or disorder in which PKCδI protein and/or RNA is up-regulated as compared to a non-diseased control as measured by a suitable assay. In some aspects, the subject can have a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative disease or a symptom thereof.

In some embodiments, the dosage forms are aerosol formulations suitable for administration by inhalation. In some of these embodiments, the aerosol formulation contains a solution or fine suspension of a compound of Formulas 1-7 or a structural analogue thereof, a PKCδ inhibitor according to any one of Formulas 1 and 3-7 or a structural analogue thereof, a PKCδI-specific inhibitor according to Formula 1 or a structural analogue thereof, auxiliary active ingredient, and/or pharmaceutically acceptable salt thereof and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof. In some aspects, the subject can have a disease or disorder in which PKCδI protein and/or RNA is up-regulated in the subject and/or adipocytes therein as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative disease or a symptom thereof.

For some dosage forms suitable and/or adapted for inhaled administration, the pharmaceutical formulation is a dry powder inhalable formulations. In addition to the a compound of Formulas 1-7 or a structural analogue thereof, a PKCδ inhibitor according to any one of Formulas 1 and 3-7 or a structural analogue thereof, a PKCδI-specific inhibitor according to Formula 1 or a structural analogue thereof, auxiliary active ingredient, and/or pharmaceutically acceptable salt thereof, such a dosage form can contain a powder base such as lactose, glucose, trehalose, manitol, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. In some aspects, the subject can have a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative disease or a symptom thereof.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets.

The parenteral formulations can be administered to a subject in need thereof. In some aspects the subject can have a disease or disorder in PKCδI protein and/or RNA is up-regulated in the subject as compared to a non-diseased control as measured by a suitable assay. In some aspects, the subject can have a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative disease or a symptom thereof.

For some embodiments, the dosage form contains a predetermined amount of a compound of any one of Formulas 1-7 or a structural analogue thereof, a PKCδ inhibitor according to any one of Formulas 1 and 3-7 or a structural analogue thereof, a PKCδI-specific inhibitor according to Formula 1 or a structural analogue thereof, auxiliary active ingredient, and/or pharmaceutically acceptable salt thereof per unit dose. In an embodiment, the predetermined amount of the compound of Formulas 1-7 or a structural analogue thereof, a PKCδ inhibitor according to any one of Formulas 1 and 3-7 or a structural analogue thereof, a PKCδI-specific inhibitor according to Formula 1 or a structural analogue thereof, auxiliary active ingredient, and/or pharmaceutically acceptable salt thereof can be an effective amount, a least effect amount, and/or a pharmaceutically effective amount. In some aspects, the predetermined amount can be effective, to inhibit PKCδ in a subject or adipocyte therein. In some aspects, the predetermined amount can be effective to specifically inhibit PKCδ in a subject or an adipocyte therein. In some aspects, the predetermined amount can be effective to treat, prevent, or mitigate the symptoms of diabetes, cancer, an inflammatory disease (such as osteoarthritis), obesity, insulin resistance, metabolic syndrome hepatosteatosis, a cardiovascular disease, a neurodegenerative disease or a symptom thereof.

In other embodiments, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations may be prepared by any of the methods well known in the art.

Methods of Making the Compounds of Formulas 1-7

The compounds and derivatives thereof can be synthesized via many methods generally known to those of ordinary skill in the art. The present disclosure is not intended to be limited by the particular methods of synthesizing the compounds described herein. The skilled artisan will recognize additional methods of synthesizing the compounds described herein.

Methods of Using the Pharmaceutical Formulations

Any amount pharmaceutical formulations described herein can be administered to a subject in need thereof one or more times per day, week, month, or year. In some embodiments, the pharmaceutical formulation administered contains an effective amount, a least effective amount, and/or a pharmaceutically effective amount of the compound of any one of Formulas 1-7 or a structural analogue thereof, a PKCδ inhibitor according to any one of Formulas 1 and 3-7 or a structural analogue thereof, and/or a PKCδI-specific inhibitor according to Formula 1 or a structural analogue thereof. For example, the pharmaceutical formulations can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the compounds, formulations, or salts thereof are administered one or more times per month, such as 1 to 5 times per month. In still further embodiments, the compounds, formulations, or salts thereof are administered one or more times per year, such as 1 to 11 times per year. a neurodegenerative disease.

In some embodiments, the subject in need thereof to which the pharmaceutical formulation is administered to can have a disease or disorder in PKCδI protein and/or RNA is up-regulated in the subject as compared to a non-diseased control as measured by a suitable assay. In some aspects, the subject can have a disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc. Other suitable assays will be appreciated by those of ordinary skill in the art. In some embodiments, the subject in need thereof can have diabetes, cancer, an inflammatory disease (such as osteoarthritis), obesity, insulin resistance, metabolic syndrome hepatosteatosis, a cardiovascular disease, a neurodegenerative disease or a symptom thereof.

In embodiments where more than one of compounds, formulations, additional therapeutic agents, salts thereof, or pharmaceutically acceptable salts thereof are administered to a subject in need thereof sequentially; the sequential administration may be close in time or remote in time. For example, administration of the second compound, formulation, or other therapeutic agent can occur within seconds or minutes (up to about 1 hour) after administration of the first agent (close in time). In other embodiments, administration of the second compound, formulation, or other therapeutic agent occurs at some other time that is more than an hour after administration of the first agent.

The amount of pharmaceutical formulations described herein can be administered in an amount ranging from about 0.01 mg to about 1000 mg per day, as calculated as the free or unsalted compound having a structure according to any of Formulas 1-7 or structural analogue thereof.

The pharmaceutical formulations provided herein can be administered in combinations with or include one or more other auxiliary agents. Suitable auxiliary agents include, but are not limited to antisense or RNA interference molecules, chemotherapeutics, anti-neoplasic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

Kits

The pharmaceutical formulations provided herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions can provide directions for administering the compounds, pharmaceutical formulations, or salts thereof to a subject having a disease or disorder in PKCδI protein and/or RNA is up-regulated in the subject as compared to a non-diseased control as measured by a suitable assay. In some aspects, the instructions can provide directions for administering the compounds, pharmaceutical formulations, or salts thereof to a subject having disease or disorder in which PKCδI protein and/or RNA is up-regulated in adipocytes from the subject as compared to a non-diseased control as measured by a suitable assay. Suitable assays for determining if PKCδI protein and/or is up-regulated include, but are not limited to, RT-PCR, qRT-PCR, ELISA, western blot, mass-spectrometry, flow cytometry, RNA sequencing, etc.

Other suitable assays will be appreciated by those of ordinary skill in the art. the instructions can provide directions for administering the compounds, pharmaceutical formulations, or salts thereof to a subject having diabetes, cancer, an inflammatory disease (such as osteoarthritis), obesity, insulin resistance, metabolic syndrome hepatosteatosis, a cardiovascular disease, a neurodegenerative disease or a symptom thereof.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

PKCδI is a key kinase that is upregulated in several medical conditions, including diabetes, cancer, osteoarthritis, hepatosteatosis, cardiovascular diseases, and metabolic syndrome.

Protein kinase C (PKC), a serine/threonine kinase family, contains 11 isoforms and their splice variants and is involved in the regulation of cellular differentiation, growth and apoptosis. The primary amino acid structure of PKCs can be divided into conserved regions (C1-C4) separated by the variable regions (V1-V5). It's regulatory and catalytic domain are separated by a hinge region. All PKCs have an N-terminal regulatory domain and a C-terminal catalytic domain separated by the V3 hinge region. Activation of PKCs can be accomplished in two ways: upon binding of activating factors like calcium, phosphatidyl serine, diacyl glycerol or phorbol esters, the pseudosubstrate region (present in the regulatory domain) is released from the substrate binding pocket and the catalytic domain is thereby activated. PKCs can also be activated by proteolytic cleavage at the V3 hinge region by calpain I, II or caspase-3 to generate a constitutively active catalytic domain of PKC (1, 2). Protein kinase Cδ is proteolytically cleaved at the V3 hinge domain in response to apoptotic stimuli by caspase 3 (3-5). The release of the catalytically active fragment induces nuclear fragmentation and cell apoptosis in various cell types including dopaminergic neuronal cell lines (6). Furthermore, inhibition of the catalytic fragment of PKCδ abrogates caspase-induced apoptosis (7). The V3 or hinge region of PKCδ contains the caspase-3 recognition sequence, DXXD (P4–P1)/X. The cleavage and activation of PKCδ sets up a positive feedback loop that impinges upon more upstream components of the death effector pathway, thereby amplifying the caspase cascade and helping cells commit to apoptosis (8). It was shown that PKCδ catalytic fragment by itself induces apoptosis and activates caspases in the intrinsic death effector pathway in human keratinocytes (9, 10).

There are several alternatively spliced variants of PKCδ (PRKCD). The expression of PKCδ splice variants is species-specific. PKCδI is ubiquitously present in all species while PKCδII, -δIV, -δV, -δVI and -δVII isoforms are present in mouse tissues (11, 12) and PKCδIII is present in rats (13).

PKCδI, referred to as PKCδ in most literature, is the pro-apoptotic splice variant. We have shown that PKCδII (mouse splice variant) and PKCδVIII (human splice variant) function as pro-survival proteins (14, 15); the functions of other PKCδ splice variants are not yet established. PKCδI plays a central role in promoting apoptosis. It is a substrate for and activator of caspase-3 (16), indicating a positive feedback loop between the two enzymes (17). In response to apoptotic stimuli, PKCδI is proteolytically cleaved at the V3 hinge domain by caspase 3 (3-5). The release of the catalytically active fragment induces nuclear fragmentation and apoptosis in various cell types, including dopaminergic neuronal cell lines (6). Further, caspase-induced apoptosis is blocked by inhibiting the catalytic fragment of PKCδI (7).

In this Example, small molecules that can be capable of inhibiting a PKC are demonstrated. To identify candidate small molecules, various compounds were docked in the active site of PKCδI on the C2 domain. Compounds that also simultaneously bound to the DMQD amino acid sequence within the V3 hinge region of PKCδI, which can increase the specificity of the compounds to inhibit PKCδI, were also identified.

Results

The process of designing a computational model for membrane proteins is challenging. The use of Schrodinger PRIME software was used to perform homology modeling of various PKC isoforms available on the PDB including 4RA5 (Human Protein Kinase C THETA IN COMPLEX WITH LIGAND COMPOUND 11a (6-[(1,3-Dimethyl-azetidin-3-yl)-methyl-amino]-4(R)-methyl-7-phenyl-2,10-dihydro-9-oxa-1,2,4a-triaza-phenanthren-3-one)), 2JED (The crystal structure of the kinase domain of the protein kinase C theta in complex with NVP-XAA2288 at 2.23A resolution), and 2IOE (Structure of the catalytic domain of human protein kinase C beta II complexed with a bisindoylmaleimide inhibitor) were utilized to create computational chimeras to establish a suitable protein scaffold for docking. These structure were then minimized using the Schrodinger Protein Preparation Wizard and the OPLS 2005 forcefields. De novo protein predictions were also prepared and minimized using Protein Preparation Wizard from Zhang lab at University of Michigan and RaptorX, which are publically available online tools.

These models were then docked using a variety of chemical libraries. All of the results were then culled together in a spreadsheet and statistical weights were placed on the various models based upon chemical intuition that allowed for predicting compounds that would have the highest probability of pharmacological success based on the protein docking scheme devised. The protein docking scheme took advantage of key amino acid residues that were determined to allow specificity with respect to PKCd1 allowing these compounds to target this isoform in predominance over the other forms of PKC. These compounds were computationally determined to show affinity to the DMQD region of PKC in the various models that were prepared. Docking was performed using Schrodinger GLIDE XP. One such model is shown in FIG. 1, which demonstrates compound 5320091 (Formula 3) docked to the DMQD region of PKCd1 depicted in green.

Identified compounds from the protein docking models were compounds having formulas according to Formulas 1-7.

Formula 1

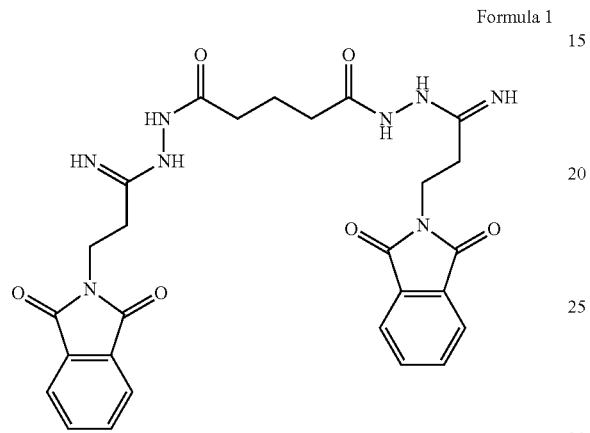

Formula 2

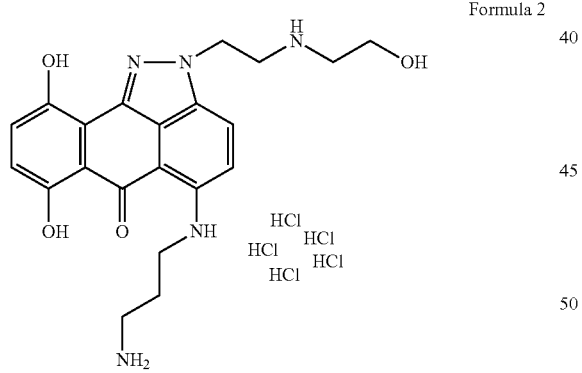

Formula 3

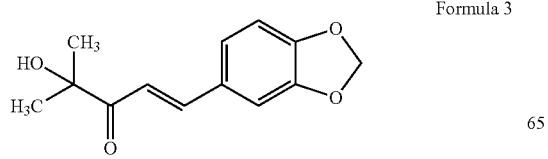

Formula 4

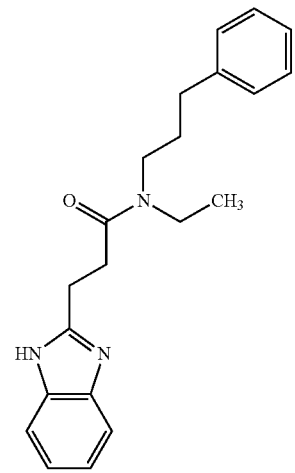

Formula 5

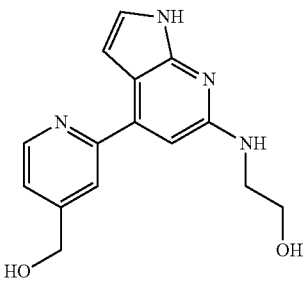

Formula 6

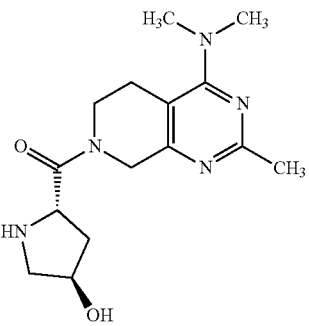

Formula 7

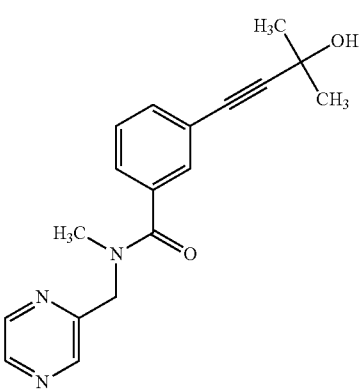

TABLE 1

Identified Compounds

| Formula | Chembridge ID | Chemical Name | Formula | Molecular Weight |
|---|---|---|---|---|
| 1 | 5139627 | N'~1~,N'~5~-bis[3-(1,3-dioxo-1,3-dihydro-2H-isoindol-2-yl)propanimidoyl]pentanedihydrazide | $C_{27}H_{25}N_8O_6$ | 561 |
| 2 | 5358118 | 5-[(3-aminopropyl)amino]-7,10-dihydroxy-2-{2-[(2-hydroxyethyl)amino]ethyl}dibenzo[cd,g]indazol-6(2H)-one pentahydrochloride | $C_{21}H_{25}N_5O_{4.5}ClH$ | 594 |
| 3 | 5320091 | 1-(1,3-benzodioxol-5-yl)-4-hydroxy-4-methyl-1-penten-3-one | $C_{13}H_{14}O_4$ | 234 |
| 4 | 72950115 | 3-(1H-benzimidazol-2-yl)-N-ethyl-N-[(2E)-3-phenylprop-2-en-1-yl]propanamide | $C_{21}H_{23}N_3O$ | 333 |
| 5 | 28578828 | 2-({4-[4-(hydroxymethyl)pyridin-2-yl]-1H-pyrrolo[2,3-b]pyridin-6-yl}amino)ethanol | $C_{15}H_{16}N_4O_2$ | 284 |
| 6 | 61397826 | (3R,5S)-5-{[4-(dimethylamino)-2-methyl-5,8-dihydropyrido[3,4-d]pyrimidin-7(6H)-yl]carbonyl}-3-pyrrolidinol | $C_{15}H_{23}N_5O_2$ | 305 |
| 7 | 43844983 | 3-(3-hydroxy-3-methylbut-1-yn-1-yl)-N-methyl-N-(pyrazin-2-ylmethyl)benzamide | $C_{18}H_{19}N_3O_2$ | 309 |

The compounds identified from the docking modeling were tested for their ability to inhibit PKCδI. 3T3L1 cells were plated in 60 mm dishes and differentiated. PKCδI regulates cell cycle during differentiation of pre-adipocytes to adipocytes. The inhibitors were added on day 1 of differentiation during mitotic clonal expansion when PKCδI expression is high (18). After 24 h, the cells were harvested and western blot analysis was performed on whole cell lysates. Using a C-terminal PKCδ antibody, it was demonstrated that the compounds 5139627, 5320091, 72950115, 28578828, 61397826 and 43844983 can inhibit the cleavage and release of the PKCδI catalytic domain. The compounds did not decrease PKCδII expression. The results demonstrate decreased phosphorylation of myelin basic protein, a known PKCδI substrate in the presence of the compounds 5320091, 72950115, 28578828, 61397826 and 43844983.

Figure 2:
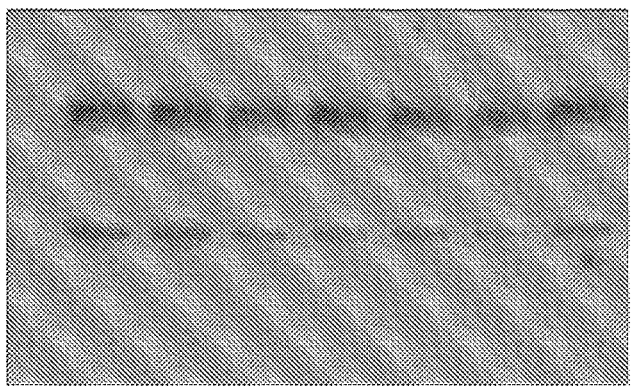
FIG. 2 shows a representative western blot, which examines the effects of various compounds on the cleavage and release of the PKCδI catalytic domain and phosphorylation of myelin basic protein (MBP).
Figure 2:
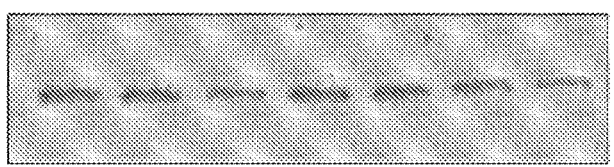

Next, compounds 5139627, 5320091, 72950115, 28578828, 61397826 and 43844983 were tested on mature adipocytes. The inhibitors were added on day 6 of differentiation when the adipocytes are lipid laden. After 24 h, the cells were harvested and western blot analysis was performed on whole cell lysates. Results are shown in FIG. 2. The results demonstrate decreased phosphorylation of myelin basic protein, a known PKCδI substrate in the presence of the compounds 5139627, 5320091, 72950115, 28578828, 61397826 and 43844983. Using a C-terminal PKCδ antibody, it was demonstrated that the compounds 5139627, 5320091, 72950115, 28578828, 61397826 and 43844983 inhibited the cleavage and release of the PKCδI catalytic domain. The compounds did not decrease PKCδII expression. Compound 43844983 appeared to completely inhibit PKCδI cleavage and phosphorylation of MBP in both pre-adipocytes and mature adipocytes; the other compounds inhibited cleavage of PKCδI and phosphorylation of MBP by over 85%.

Figure 3:
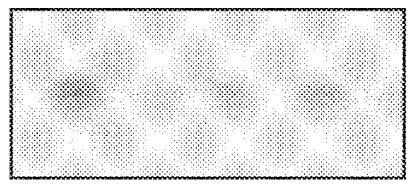
FIG. 3 shows a blot demonstrating the results of an in-vitro kinase assay evaluating the effect of compounds on PKCδI activity.

Next, in vitro kinase assays were performed with recombinant proteins PKCδI and SC35 (as substrate) in a kinase buffer containing phosphatidyl serine and ATP; with and without 10 nM 5139627, 28578828 (30 min incubation prior to assay). Representative results are shown in FIG. 3. It was demonstrated that at least 5139627, 28578828, can specifically inhibit PKCδI activity.

Figure 4:
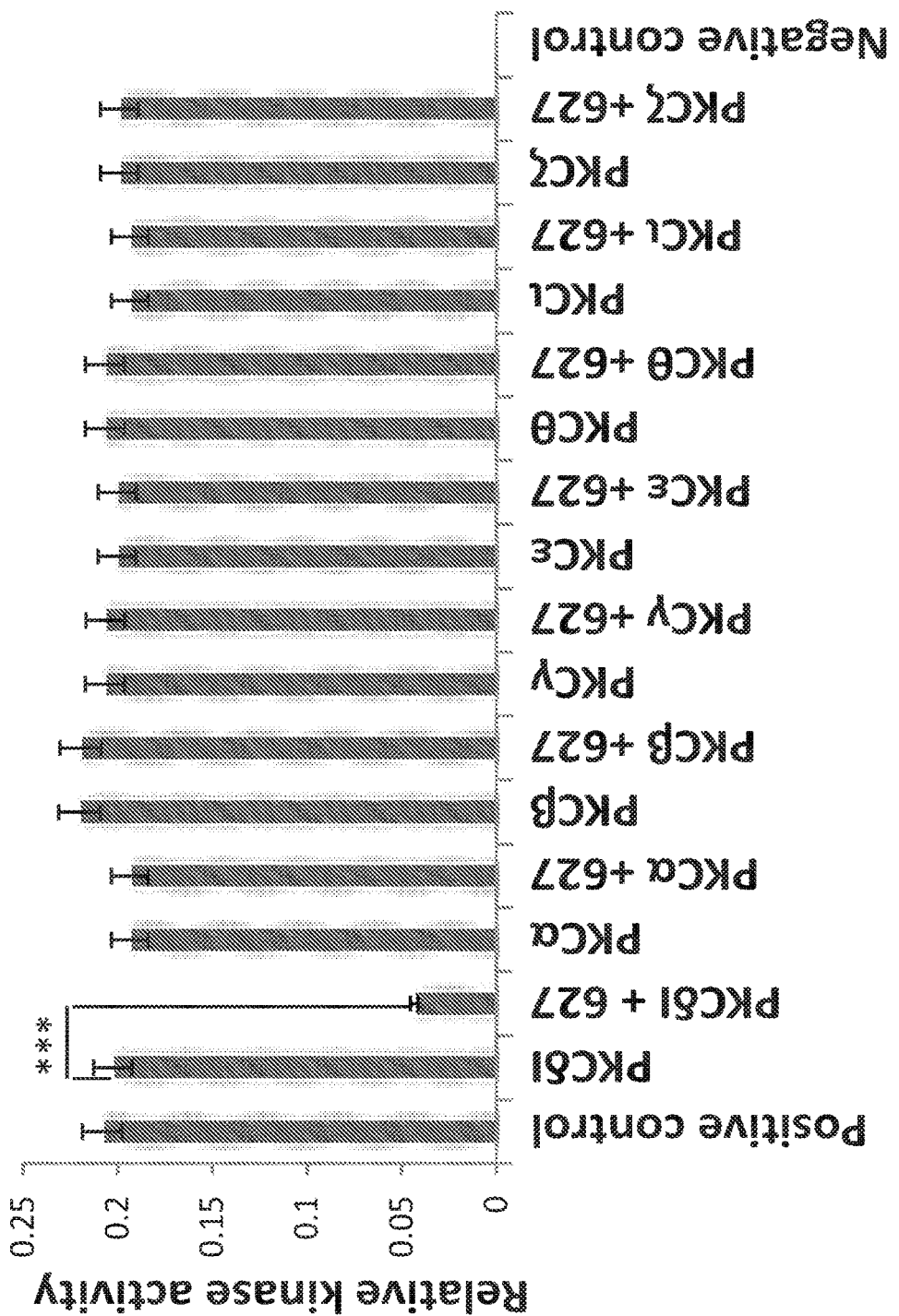
FIG. 4 shows a graph demonstrating the effect of compound 5139627 on the activity of various PKCs.

Next it was validated that 5139627 does not affect the activity of other PKCs, and thus can specifically inhibit PKCδI. Briefly, a Protein Kinase C (PKC) kinase activity kit was used and a colorimetric assay (ENZO; run in triplicate) was performed. Relative kinase activity was calculated as (average absorbance of PKC isozyme−Average absorbance of blank)/quantity of pure kinase used per assay. FIG. 4 demonstrates the results from a PKC kinase activity assay, which demonstrates that at least compound 5139627 has specificity for PKCδI and that other PKC isozyme activities were not inhibited by 5139627.

Figure 5:
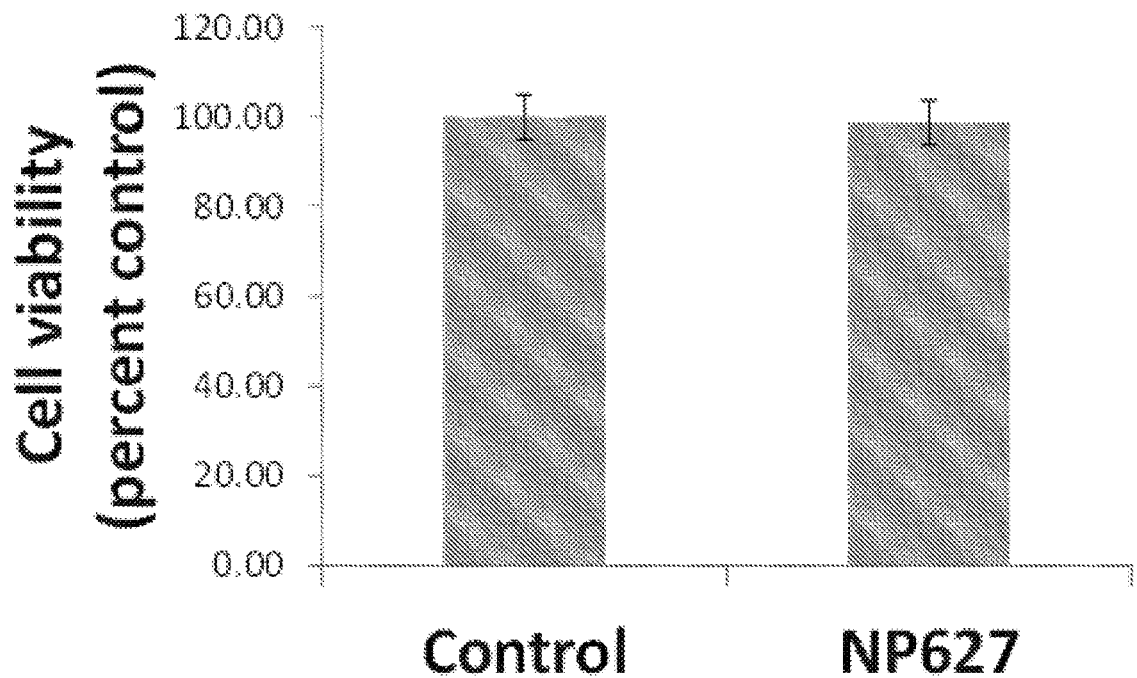
FIG. 5 shows a graph demonstrating the effect of compound 5139627 on apoptosis in adipocytes.

A WST-1 assay performed using obese adipocytes treated with 513627 to evaluate toxicity of compound 513627. Briefly, obese adipocytes were treated with 10 nM of compound 513627 and a WST-1 assay for cell viability was performed. FIG. 5 represents data from four experiments. The data demonstrates that compound 513627 did not appear to cause cellular toxicity (FIG. 5).

Figure 6:
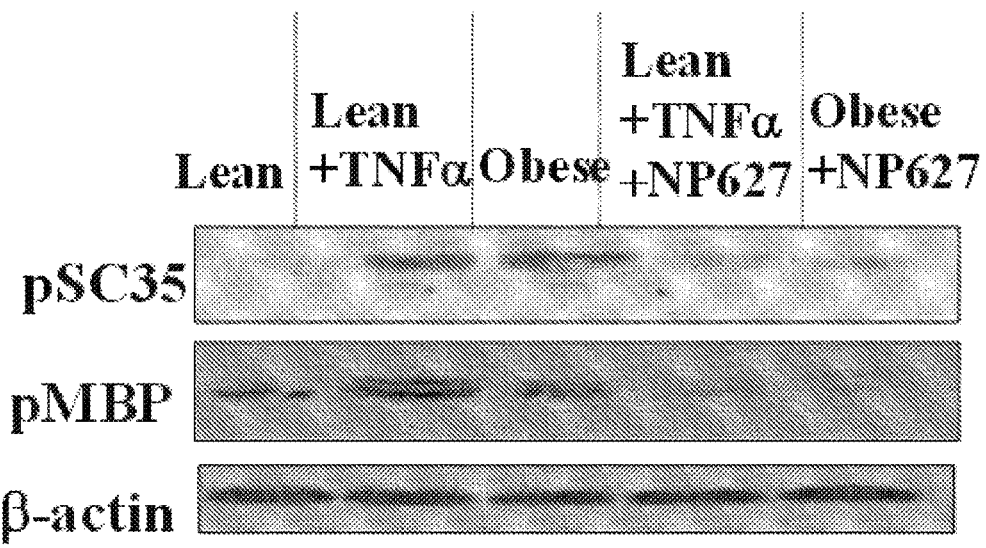
FIG. 6 shows representative PCR gel images demonstrating the effect of compound 5139627 on pSC35, pMBP, and β-actin (control) in adipocytes with and without TNFα stimulation from lean and obese subjects.

In obesity, TNFα promotes inflammation and apoptosis of adipocytes. The data can demonstrate that TNFα cleaves PKCδI. Briefly, about 100 ng TNFα was added to lean adipocytes along with about 10 nM 5139627 for 24 h. Simultaneously, obese adipocytes were treated with 10 nM 5139627 for 24 h. Last, obese adipocytes were treated with about 10 nM of compound 5139627. Expression of pSC35, phosphor-myelin basic protein (pMBP) were analyzed via western blot. B-actin expression was used as a control. Results are demonstrated in FIG. 6, which shows representative data from four experiments.

Figure 7:
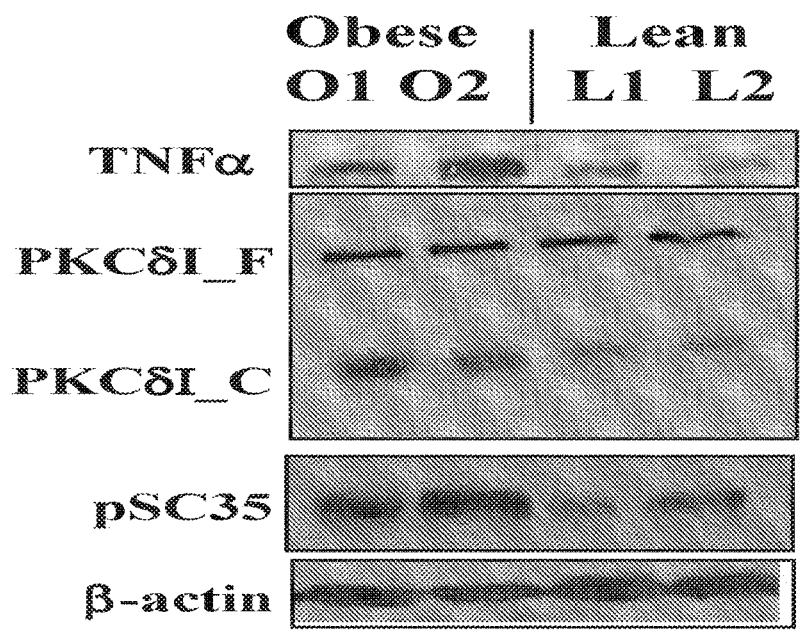
FIG. 7 shows representative blots demonstrating the effect of compound 5139627 on TNFα, PKCδI_F, PKCδI_C, pSC35, and β-actin (control) in adipocytes from lean and obese mice.

Additionally, adipocytes were isolated from lean or DIO mice. Expression of TNFα, PKCδI_F, PKCδI_C, pSC35, and β-Actin (control) was analyzed via western blotting. Results are demonstrated in FIG. 7, which shows a representative blot from six experiments (each blot shows data from 2 mice). The results can indicate that PKCδI cleavage of its C-terminal domain (necessary to mediate its pro-apoptotic and pro-inflammatory action) is increased in obesity.

Figure 8:
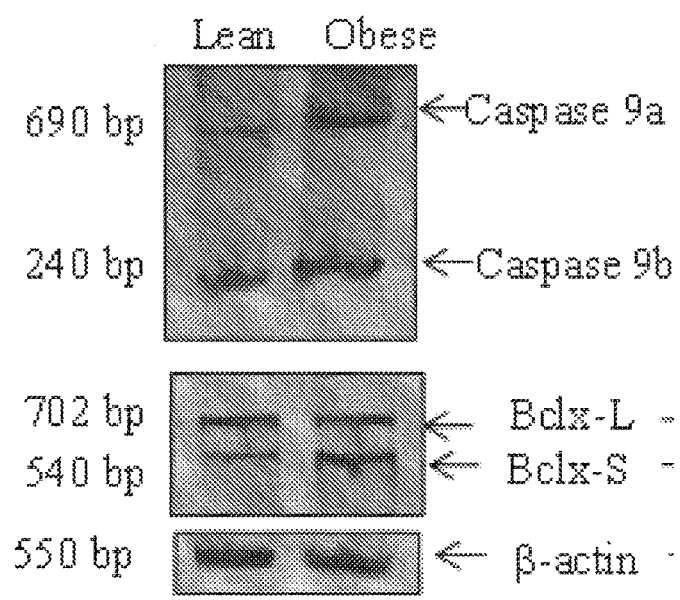
FIG. 8 shows representative blots demonstrating the effect of compound 5139627 on Caspase 9a, Caspase 9b, Bclx-L, Bclx-S, and β-actin (control) in adipocytes from lean and obese subjects.

The C-terminal fragment of PKCδI phosphorylates its substrates that mediate expression of pro-apoptotic proteins. For a functional read-out, an assay was designed to measure: (1) Bcl-xL switching to its pro-apoptotic variant Bcl-xS and (2) Caspase9b switching to its pro-apoptotic variant caspase 9a. Briefly, adipocytes were freshly isolated from human visceral adipose tissue of lean and obese donors (IRB #20295; lean BMI 22.1 and 23; obese BMI 43.7 and 44.3;

non-diabetic, nonsmokers, non-cancer). Results are shown in FIG. 8, and can demonstrate that obese adipocytes had greater expression of BclxS and caspase9a.

Figure 9:
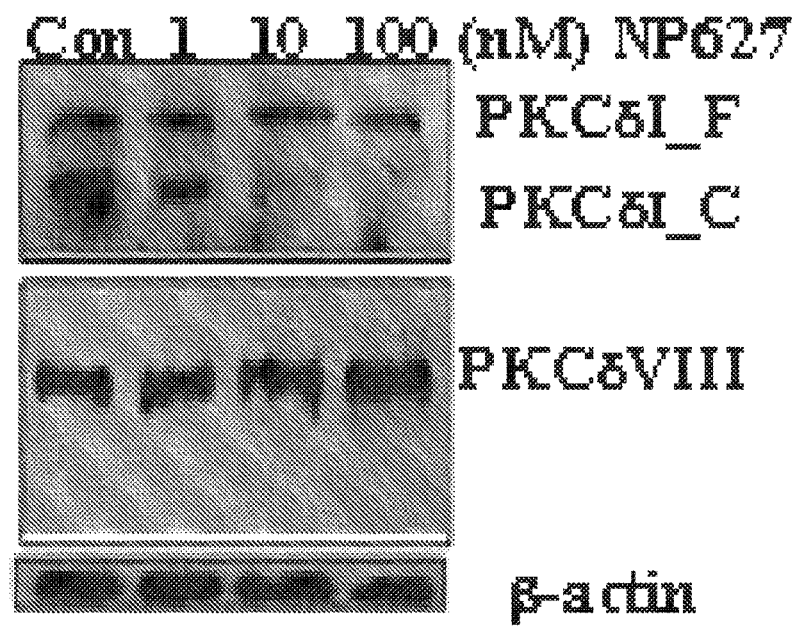
FIG. 9 shows a representative blots demonstrating the effect of various concentrations of compound 5139627 on PKCδI_F, PKCδI_C, PKCδVIII, and β-actin (control) in adipocytes.

Additionally, adipocytes from the obese donor were treated with about 10-100 nM NP627 (compound 513627) for about 24 h (n=3). Expression of PKCδI_F, PKCδI_C, PKCδVIII, and β-Actin (control) were analyzed using western blotting. Results are shown in FIG. 9, and can demonstrate that NP627 specifically inhibits cleavage of PKCδI; the alternatively spliced variant PKCδVIII is not inhibited by NP627.

Figure 10:
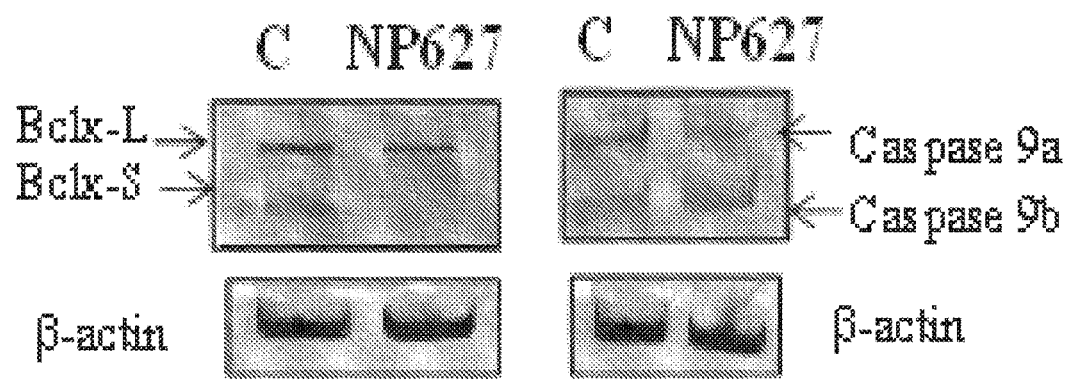
FIG. 10 shows a representative PCR gel image demonstrating the effect of compound 5139627 on expression of Caspase 9a, Caspase 9b, Bclx-L, Bclx-S, and δ-actin (control) in adipocytes from obese subjects.

Additionally, adipocytes from the obese donor were treated with about 10 nM of NP627 for about 24 h (n=3). Expression of Bxl-xL, Bxl-xS, caspase9a, andβ-actin (control) were analyzed using a PCR based technique (n=3). A representative PCR gel image is shown in FIG. 10. The results can demonstrate that NP627 can decrease expression of Bxl-xS and caspase9a.

Figure 11:
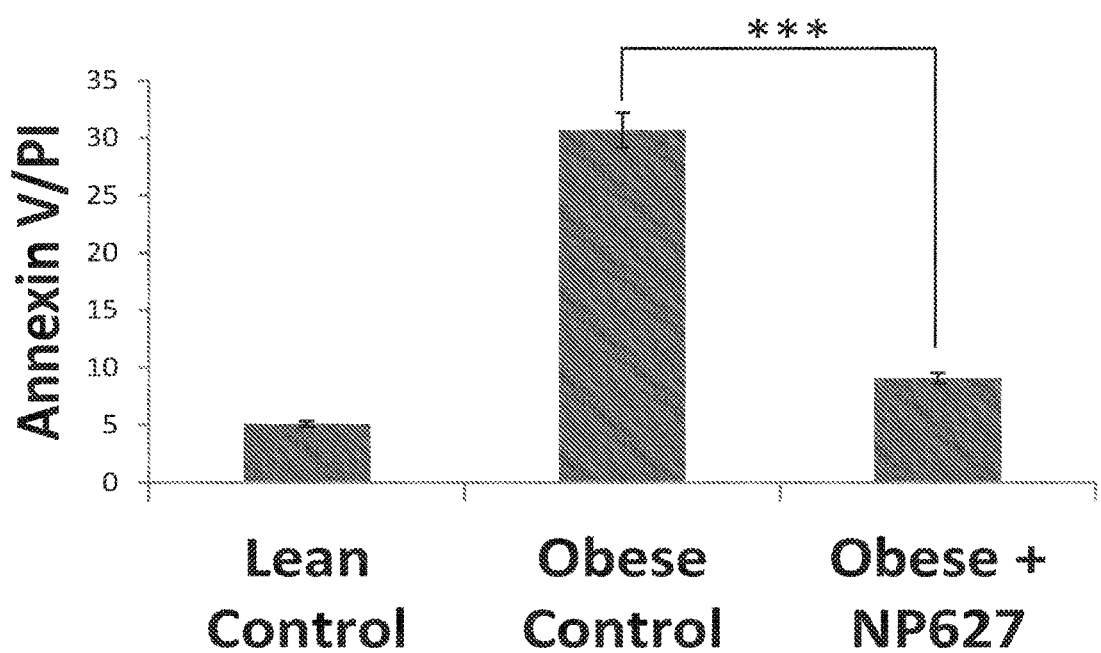
FIG. 11 shows a graph demonstrating the effect of compound 5139627 on apoptosis in adipocytes from lean and obese subjects.

Additionally, apoptosis in adipocytes from an obese subject treated with NP627 was examined using flow annexin/PI cytometry (n=3). Results are shown in FIG. 11. ***p<0.001, which is considered highly significant.

REFERENCES FROM EXAMPLE 1

1. Parker, P. J., and Murray-Rust, J. (2004) PKC at a glance. *J Cell Sci* 117, 131-132
2. Sampson, S. R., and Cooper, D. R. (2006) Specific protein kinase C isoforms as transducers and modulators of insulin signaling. *Mol Genet Metab* 89, 32-47
3. Emoto, Y., Manome, Y., Meinhardt, G., Kisaki, H., Kharbanda, S., Robertson, M., Ghayur, T., Wong, W. W., Kamen, R., Weichselbaum, R., and et al. (1995) Proteolytic activation of protein kinase C delta by an ICE-like protease in apoptotic cells. *EMBO J* 14, 6148-6156
4. Ghayur, T., Hugunin, M., Talanian, R. V., Ratnofsky, S., Quinlan, C., Emoto, Y., Pandey, P., Datta, R., Huang, Y., Kharbanda, S., Allen, H., Kamen, R., Wong, W., and Kufe, D. (1996) Proteolytic activation of protein kinase C delta by an ICE/CED 3-like protease induces characteristics of apoptosis. *J Exp Med* 184, 2399-2404
5. Kohtz, J. D., Jamison, S. F., Will, C. L., Zuo, P., Luhrmann, R., Barcia-Blanco, M. A., and Manley, J. L. (1994) Protein-protein interactions and 5-splice-site recognition in mammalian mRNA precursors. *Nature* 368, 119-124
6. Anantharam, V., Kitazawa, M., Wagner, J., Kaul, S., and Kanthasamy, A. G. (2002) Caspase-3-dependent proteolytic cleavage of protein kinase Cdelta is essential for oxidative stress-mediated dopaminergic cell death after exposure to methylcyclopentadienyl manganese tricarbonyl. *J Neurosci* 22, 1738-1751
7. Reyland, M. E., Anderson, S. M., Matassa, A. A., Barzen, K. A., and Quissell, D. O. (1999) Protein kinase C delta is essential for etoposide-induced apoptosis in salivary gland acinar cells. *J Biol Chem* 274, 19115-19123
8. Denning, M. F., Wang, Y., Tibudan, S., Alkan, S., Nickoloff, B. J., and Qin, J. Z. (2002) Caspase activation and disruption of mitochondrial membrane potential during UV radiation-induced apoptosis of human keratinocytes requires activation of protein kinase C. *Cell Death Differ* 9, 40-52
9. Sitailo, L., Tibudan, S., and Denning, M. F. (2004) Bax activation and induction of apoptosis in human keratinocytes by protein kinase C delta catalytic domain. *Jour of Investigative Dermatology*, 1-10
10. Sitailo, L. A., Tibudan, S. S., and Denning, M. F. (2006) The protein kinase C delta catalytic fragment targets Mcl-1 for degradation to trigger apoptosis. *J Biol Chem* 281, 29703-29710
11. Sakurai, Y., Onishi, Y., Tanimoto, Y., and Kizaki, H. (2001) Novel protein kinase C delta isoform insensitive to caspase-3. *Biol Pharm Bull* 24, 973-977
12. Kawaguchi, T., Niino, Y., Ohtaki, H., Kikuyama, S., and Shioda, S. (2006) New PKCdelta family members, PKCdeltaIV, deltaV, deltaVI, and deltaVII are specifically expressed in mouse testis. *FEBS Lett* 580, 2458-2464
13. Ueyama, T., Ren, Y., Ohmori, S., Sakai, K., Tamaki, N., and Saito, N. (2000) cDNA cloning of an alternative splicing variant of protein kinase C delta (PKC deltaIII), a new truncated form of PKCdelta, in rats. *Biochem Biophys Res Commun* 269, 557-563
14. Patel, N. A., Song, S., and Cooper, D. R. (2006) PKCdelta alternatively spliced isoforms modulate cellular apoptosis in retinoic-induced differentiation of human NT2 cells and mouse embryonic stem cells. *Gene Expression* 13, 73-84
15. Jiang, K., Apostolatos, A. H., Ghansah, T., Watson, J. E., Vickers, T., Cooper, D. R., Epling-Burnette, P. K., and Patel, N. A. (2008) Identification of a Novel Antiapoptotic Human Protein Kinase C delta Isoform, PKCdeltaVIII in NT2 Cells. *Biochemistry* 47, 787-797
16. Blass, M., Kronfeld, I., Kazimirsky, G., Blumberg, P. M., and Brodie, C. (2002) Tyrosine phosphorylation of protein kinase Cdelta is essential for its apoptotic effect in response to etoposide. *Mol Cell Biol* 22, 182-195
17. Brodie, C., and Blumberg, P. M. (2003) Regulation of cell apoptosis by protein kinase c delta. *Apoptosis* 8, 19-27
18. Patel, R. S., Carter, G., Cooper, D. R., Apostolatos, H., and Patel, N. A. (2014) Transformer 2beta homolog (Drosophila) (TRA2B) regulates protein kinase C deltaI (PKCdeltaI) splice variant expression during 3T3L1 preadipocyte cell cycle. *J Biol Chem* 289, 31662-31672

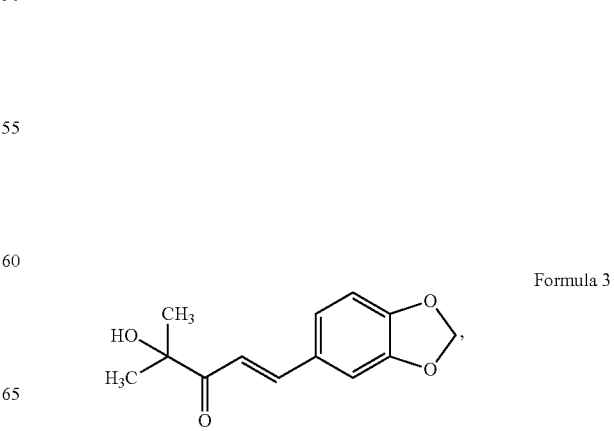

Formula 4
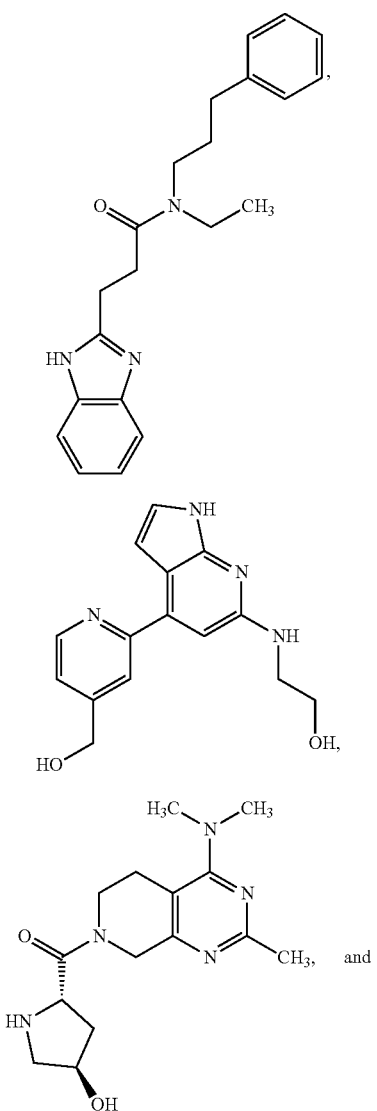
Formula 5
Formula 6
Formula 7
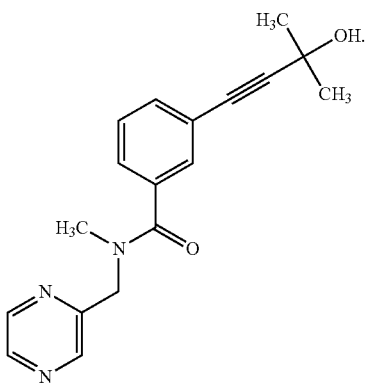
4. The method of claim 3, wherein the compound has a structure:
Formula 1
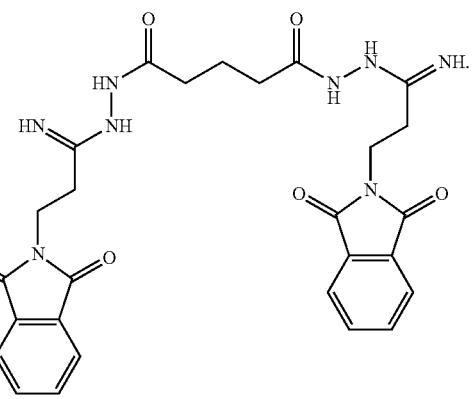

We claim:

1. A method of treating a disease or disorder associated with PKGδI activity in a subject in need thereof, wherein the disease or disorder is obesity, the method comprising administering an effective amount of a compound for inhibiting PKCδI activity in the subject, wherein the compound has a structure selected from:

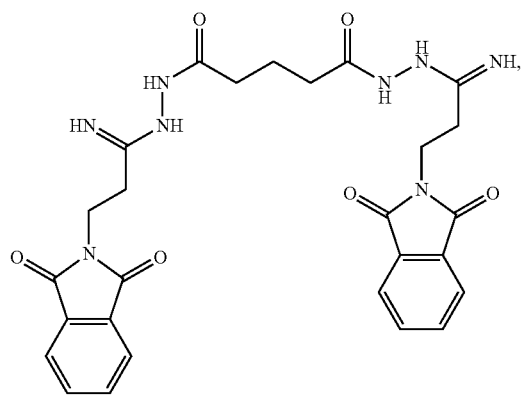

Formula 1

-continued

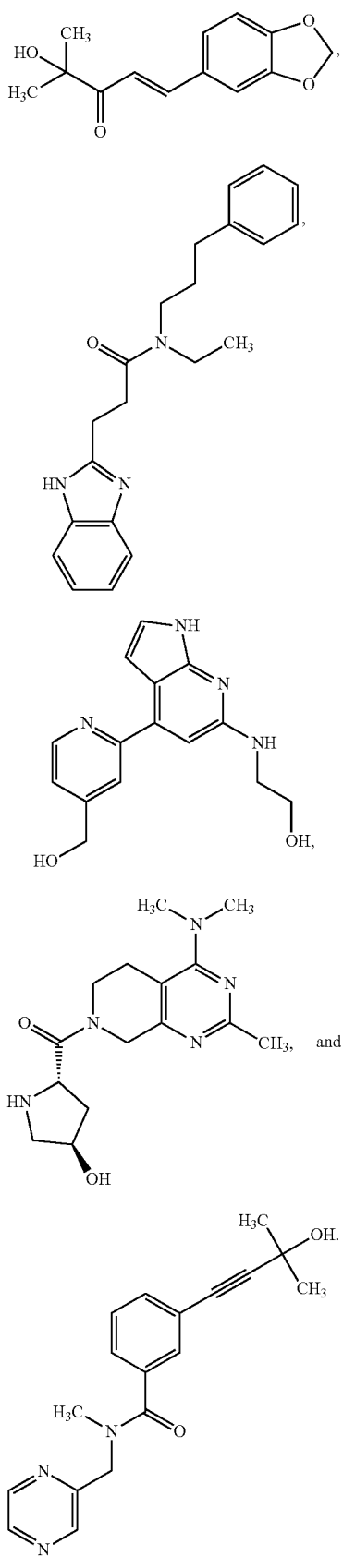

Formula 3

Formula 4

Formula 5

Formula 6

Formula 7

2. The method of claim 1, wherein the compound has a structure:

Formula 1

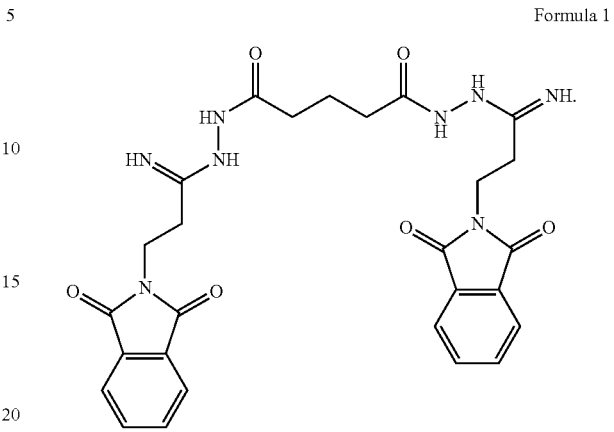

3. A method of treating obesity in a subject in need thereof, the method comprising administering an effective amount of a compound for inhibiting PKCδI activity in the subject, wherein the compound has a structure selected from:

Formula 1

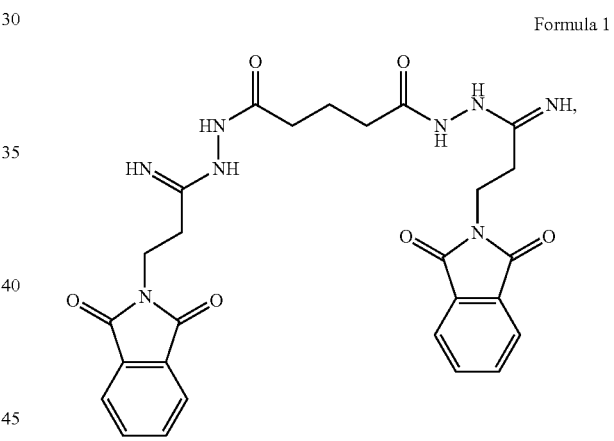

Formula 3